US010460998B2

(12) United States Patent
Fujimori

(10) Patent No.: US 10,460,998 B2
(45) Date of Patent: Oct. 29, 2019

(54) METHOD FOR INSPECTING SUBSTRATE, SUBSTRATE INSPECTION APPARATUS, EXPOSURE SYSTEM, AND METHOD FOR PRODUCING SEMICONDUCTOR DEVICE

(75) Inventor: Yoshihiko Fujimori, Yokohama (JP)

(73) Assignee: Nikon Corporation, Tokyo (JP)

( * ) Notice: Subject to any disclaimer, the term of this patent is extended or adjusted under 35 U.S.C. 154(b) by 538 days.

(21) Appl. No.: 13/291,279

(22) Filed: Nov. 8, 2011

(65) Prior Publication Data
US 2012/0122252 A1    May 17, 2012

Related U.S. Application Data

(60) Provisional application No. 61/457,400, filed on Mar. 17, 2011.

(30) Foreign Application Priority Data

Nov. 9, 2010  (JP) .................................. 2010-250428
Feb. 25, 2011 (JP) .................................. 2011-040925

(51) Int. Cl.
*H01L 21/66*   (2006.01)
*G01N 21/956*  (2006.01)

(52) U.S. Cl.
CPC ....... *H01L 22/12* (2013.01); *G01N 21/95692* (2013.01); *G01B 2210/56* (2013.01); *H01L 2924/0002* (2013.01)

(58) Field of Classification Search
CPC . H01L 22/12; H01L 22/26; G03F 1/84; G03F 7/70616; G03F 1/24; G03F 7/7065; G01N 21/95692; G01B 2210/56
(Continued)

(56) References Cited

U.S. PATENT DOCUMENTS 5,807,761 A * 9/1998 Coronel ................ B24B 37/013
                                                  204/192.13
6,226,079 B1  5/2001 Takeda et al.
(Continued)

FOREIGN PATENT DOCUMENTS

CN    101506962 A    8/2009
JP    57-206042     12/1982
(Continued)

OTHER PUBLICATIONS

International Search Report, from the Japanese Patent Office in corresponding PCT Application No. PCT/JP2011/075824, dated Mar. 13, 2012.
(Continued)

*Primary Examiner* — Khiem D Nguyen
(74) *Attorney, Agent, or Firm* — Finnegan, Henderson, Farabow, Garrett & Dunner, L.L.P.

(57) ABSTRACT

There is provided a method for inspecting a substrate including: irradiating an illumination light onto a first surface or a second surface opposite to the first surface, of a substrate in which a pattern having a periodicity and extending from the first surface to an inside of the substrate is formed in the first surface, the illumination light having a permeability to permeate the substrate to a predetermined depth; detecting a light reflected from or transmitted through the substrate due to irradiation of the illumination light; and inspecting the substrate by utilizing information based on the periodicity of the pattern obtained from detection of the light reflected from or transmitted through the substrate.

31 Claims, 16 Drawing Sheets

(58) Field of Classification Search
USPC ............... 438/14, 16; 356/237.3, 237.4; 257/E21.529, E21.527, E21.528, E21.53
See application file for complete search history.

(56) References Cited

U.S. PATENT DOCUMENTS

| | | | |
|---|---|---|---|
| 6,266,137 | B1 | 7/2001 | Morinaga |
| 6,396,944 | B1* | 5/2002 | Kung ..................... G03F 1/30 382/144 |
| 6,636,824 | B1* | 10/2003 | Sawai ................. G01R 31/307 257/E21.53 |
| 6,696,679 | B1* | 2/2004 | Graef et al. ............... 250/201.4 |
| 7,298,471 | B2 | 11/2007 | Fukazawa et al. |
| 2004/0246476 | A1* | 12/2004 | Bevis .................. G01N 21/474 356/237.5 |
| 2005/0239223 | A1* | 10/2005 | Mantz .................... G01N 21/55 438/14 |
| 2005/0258365 | A1* | 11/2005 | Bloess .................... H01L 22/12 250/309 |
| 2006/0192953 | A1* | 8/2006 | Fukazawa ............. G01B 11/30 356/237.5 |
| 2007/0076195 | A1* | 4/2007 | Yamaguchi ........ G01N 21/8806 356/237.1 |
| 2007/0148792 | A1 | 6/2007 | Marks et al. |
| 2008/0055574 | A1* | 3/2008 | Kamono ................ G01N 21/21 355/30 |
| 2008/0297784 | A1* | 12/2008 | LeBlanc ............. G01N 21/896 356/239.1 |
| 2008/0311486 | A1* | 12/2008 | Itoh ....................... B82Y 10/00 430/5 |
| 2009/0202621 | A1 | 10/2009 | Saito et al. |
| 2009/0262621 | A1* | 10/2009 | Saito et al. ................ 369/53.41 |
| 2010/0007872 | A1* | 1/2010 | Isozaki .................. G01N 21/47 356/51 |
| 2010/0165095 | A1* | 7/2010 | Nakamura ......... G01N 21/3563 348/92 |
| 2011/0042795 | A1* | 2/2011 | Knickerbocker ..... H01L 21/486 257/686 |

FOREIGN PATENT DOCUMENTS

| | | |
|---|---|---|
| JP | 58-086737 | 5/1983 |
| JP | S58-86737 | 5/1983 |
| JP | H07-294422 | 11/1995 |
| JP | 11-271233 | 10/1999 |
| JP | 2002-006226 | 1/2002 |
| JP | 2007-526444 | 9/2007 |
| JP | 2009-257993 | 11/2009 |
| JP | 2010-8392 | 1/2010 |
| WO | WO 2005/040776 A1 | 5/2005 |

OTHER PUBLICATIONS

The State Intellectual Property of P.R. China, First Office Letter dated Feb. 16, 2015 for "Method for Inspecting Pattern with Through Holes by Utilizing Infrared," for Chinese Application No. 201180053877.1.
International Preliminary Report on Patentability dated May 14, 2013, in International Application No. PCT/JP2011/075824.
Notice of Reasons for Refusal for Japasnese Patent Application No. 2012-542952 dated Apr. 8, 2015.
Second Office Letter dated Dec. 4, 2015, in corresponding Chinese Patent Application No. 201180053877.1.
Second Office Letter issued by The State Intellectual Property Office of P.R. China in counterpart Chinese Patent Application No. 2011-80053877.1, dated Dec. 4, 2015 (21 pages).
Notification of Reasons for Rejection issued by Japanese Patent Office in counterpart Japanese Patent Application No. 2012-542952, dated Feb. 9, 2016 (6 pages).
Office Action (Preliminary Examination Report) in corresponding Taiwanese Patent Application No. 10014099, dated Aug. 7, 2015.
Office Action issued by the State Intellectual Property Office of People's Republic of China in Chinese Patent Application No. 201180053877.1 dated May 16, 2016, and English translation thereof.
Office Action issued by the Korean Intellectual Property Office on Oct. 30, 2017 in counterpart Korean Application No. 10-2013-7011992, and English translation thereof.
Office Action issued by the Korean Intellectual Property Office on Sep. 28, 2018 in counterpart Korean Patent Application No. 10-2013-7011992, and English Translation thereof.

* cited by examiner

Fig. 7

| ENTRANCE LENGTH ($\mu$m) (INTENSITY 1/10) | WAVELENGTH (nm) |
|---|---|
| 1 | 623 |
| 5 | 714 |
| 10 | 754 |
| 20 | 793 |
| 30 | 816 |
| 40 | 833 |
| 50 | 845 |

METHOD FOR INSPECTING SUBSTRATE, SUBSTRATE INSPECTION APPARATUS, EXPOSURE SYSTEM, AND METHOD FOR PRODUCING SEMICONDUCTOR DEVICE

CROSS REFERENCE TO RELATED APPLICATIONS

The present application claims priority from U.S. Provisional Patent Application No. 61/457400 filed on Mar. 17, 2011 and claims priority from Japanese Patent Application Nos. 2010-250428 and 2011-040925 filed respectively on Nov. 9, 2010 and on Feb. 25, 2011, all the disclosures of which are incorporated herein by reference in their entirety.

BACKGROUND

Field of the Invention

The present teaching relates to a method for inspecting a substrate and a substrate inspection apparatus utilized for three-dimensional lamination and the like. The present teaching further relates to an exposure system and a method for producing semiconductor devices utilizing the inspection method and the inspection apparatus.

Description of the Related Art

As the miniaturization of semiconductors is said to be approaching its limit, three-dimensional lamination of semiconductor chips has the advantages in improving performance, saving power, saving space, and the like. Hence, it is rapidly spreading as a means for increasing added value abreast with the miniaturization of semiconductors. The three-dimensional lamination is a technique for laminating semiconductor chips which have been made as thin as approximately 10 to 50 µm. The upper and lower chips are electrically connected by a plurality of electrodes through the chips (TSV: Through-Silicon Via). In this manner, because it is possible to electrically connect the chips in a short distance, compared with the conventional SIP (System in a Package) connecting the chips aligned horizontally, increasing the working speed of elements, and saving the power and space can be achieved.

There are various methods for forming TSVs. For example, the TSVs may be formed either before or after the elements in a semiconductor chip are formed. However, in either case, the TSVs are formed by making deep and fine holes in a wafer (a silicon substrate), covering the sidewall of the holes with an insulating film, and then filling up the holes with a highly-conductive substance such as copper and the like. At the time, it is important to inspect the wafer during and after forming the TSVs. These inspections are carried out by breaking up the wafer to observe the wafer with a SEM (Scanning Electron Microscope) or a TEM (Transmission Electron Microscope). Although it is possible to observe the actual shape of the cross section with this method, the inspection is destructive and time-consuming.

On the other hand, there is another method which utilizes a microscope and the like to observe the wafer surface. However, in this manner it is merely possible to confirm the state of the wafer surface. Further, although microscopes utilizing infrared light are also applied to observe the transmission image, because the region observable at one time is extremely small, it is impractical to inspect the TSVs of the entire wafer surface with this method. Further, because the transmission image from one side is observed, it is difficult to detect a minute and tridimensional change in profile with this method.

However, there is a technique for inspecting the repetitive pattern formed in a semiconductor wafer by detecting intensity of diffracted light, changes in polarized state, and the like (see U.S. Pat. No. 7,298,471, for example). According to this method, it is possible to inspect a large area in a short time, and detect abnormities, with a high sensitivity in a short time, due to the focus variation or dose (exposure energy) variation of the exposure device for forming the pattern as well as abnormities due to the malfunction or maladjustment of the processing device.

SUMMARY

According to an aspect of the present teaching, there is provided a method for inspecting a substrate including:

irradiating an illumination light onto a first surface or a second surface opposite to the first surface, of a substrate in which a pattern having a periodicity and extending from the first surface to an inside of the substrate is formed in the first surface, the illumination light having a permeability to permeate the substrate to a predetermined depth;

detecting a light reflected from or transmitted through the substrate due to irradiation of the illumination light; and inspecting the substrate by utilizing information based on the pattern obtained from detection of the light reflected from or transmitted through the substrate.

BRIEF DESCRIPTION OF THE DRAWINGS

FIG. 7 is a table showing a relationship between the entrance length into silicon and light wavelength;

DESCRIPTION OF THE EMBODIMENTS

Figure 2:
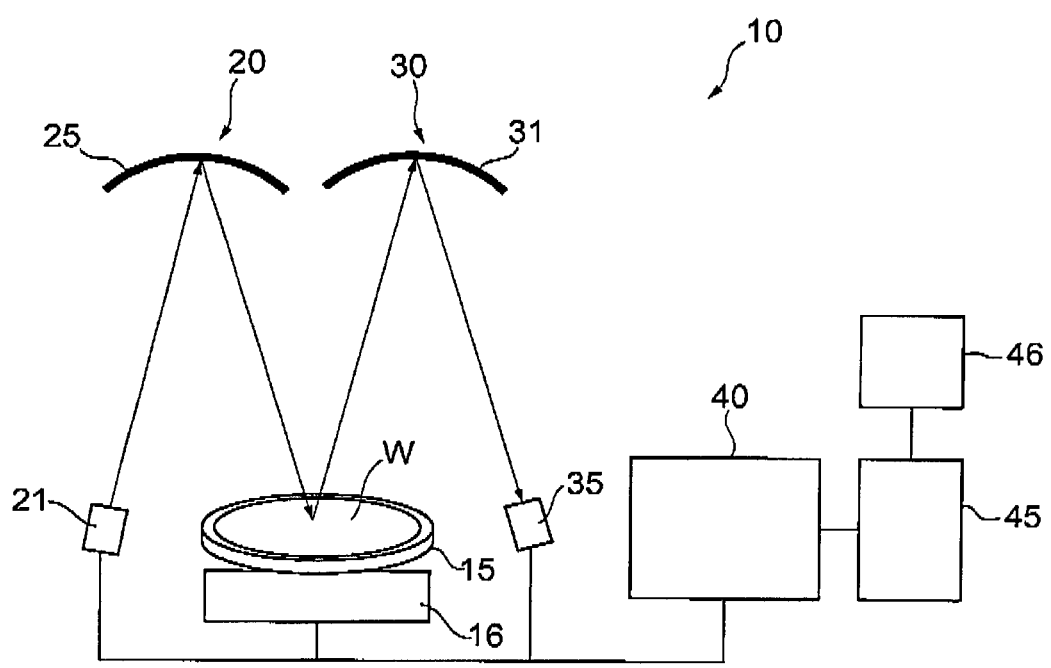
FIG. 2 is a schematic configuration diagram of an inspection apparatus.

Hereinbelow, referring to the accompanying drawings, explanations will be made with respect to embodiments of the present teaching. FIG. 2 shows an inspection apparatus in accordance with a first embodiment for inspecting the entire surface of a wafer W which is a silicon substrate, all at one time. The inspection apparatus 10 of the first embodiment includes a wafer holder 15 which holds the approximately disk-shaped wafer W transported by a transport unit (not shown). The wafer W is placed on the wafer holder 15 and is fixed through vacuum suction. By means of a rotating and tilting mechanism 16, the wafer W held on the wafer holder 15 is rotatable with respect to a symmetrical axis as the rotation axis of the wafer W (the central axis of the wafer holder 15). Further, still by means of the rotating and tilting mechanism 16, it is possible to tilt (incline) the wafer W held on the wafer holder 15 about an axis through the surface of the wafer W, and thereby the incidence angle of illumination light is adjustable.

The inspection apparatus 10 is configured to further include an illumination system 20 (an irradiation section) which irradiates illumination light as parallel light onto the surface of the wafer W held on the wafer holder 15, a light receiving system 30 which condenses or focuses the light from the wafer W that is reflected by the wafer W when the irradiated illumination light is received, an imaging device 35 (a detection section) which takes an image of the wafer W by receiving the light condensed by the light receiving system 30, a controller 40 (an adjustment section), and an image processing section 45 (an inspection section). The illumination system 20 is configured to have a light source 21 which emits illumination light, and an illumination-side concave mirror 25 which reflects the illumination light emitted from the light source 21 toward the surface of the wafer W. The light source 21 includes a halogen lamp and the like, and is capable of emitting a light beam selected from a plurality of wavelengths, which will be described in detail hereinafter, by utilizing a plurality of wavelength selection filters (not shown). Further, other than wavelength selection filters, a spectrometer can be utilized to select the wavelength of illumination light.

Then, because the emission portion of the light source 21 is arranged on the focal plane of the illumination-side concave mirror 25, the illumination light emitted from the light source 21 to the illumination-side concave mirror 25 then becomes parallel (telecentric) light to be irradiated onto the entire surface of the wafer W held on the wafer holder 15. Further, the incoming and outgoing angles of the illumination light to and from the wafer W are adjustable by tilting (inclining) the wafer holder 15 to change the angle at which the wafer W is placed.

The light receiving system 30 condenses the outgoing lights from the wafer W (the diffracted light, the specular light, and the like). The light receiving system 30 mainly includes a light-receiving-side concave mirror 31 arranged to face the wafer holder 15. The outgoing lights condensed by the light-receiving-side concave mirror 31 come onto the imaging plane of the imaging device 35 to form an image of the wafer W. The imaging device 35 includes an objective lens, an image sensor and the like (not shown). The imaging device 35 generates an image signal (a detection signal) by photoelectrically converting the image of the wafer W formed on the imaging plane of the image sensor, and outputs the generated image signal to the image processing section 45 via the controller 40.

The controller 40 controls the operations of the wafer holder 15, the rotating and tilting mechanism 16, the light source 21, the imaging device 35 and the like, respectively. Further, in order to satisfy an aftermentioned diffraction condition, the controller 40 is configured to adjust at least one of the wafer holder 15, the rotating and tilting mechanism 16, the light source 21, and the imaging device 35. The image processing section 45 generates a digital image for the wafer W based on the image signal of the wafer W inputted from the imaging device 35. A database 46 electrically connected to the image processing section 45 previously stores the image data of a nondefective wafer. When the image processing section 45 generates an image for the wafer W (a digital image), the image processing section 45 compares the generated image data of the wafer W with the image data of a nondefective wafer stored in the database 46 to inspect whether or not there is any abnormality (defection) in the wafer W. Then, the inspection result from the image processing section 45 and the image of the wafer W are outputted and displayed on an image display device (not shown). Further, it is not necessary to electrically connect the database 46 and the image processing section 45 but possible to connect them through a wireless system, for example, such that the information is transmittable.

However, the wafer W which is an object of the inspection is transported by the transporting device (not shown) from a processing device (an etching device, for example) to the wafer holder 15 after an inspection object process (an etching process, for example). At the time, the inspection object wafer W is transported to the wafer chuck 15 after an alignment is made based on the pattern of the wafer W or based on a positional reference which is provided on the outer edge of the wafer W (a notch, an orientation flat, or the like).

Figure 3A:
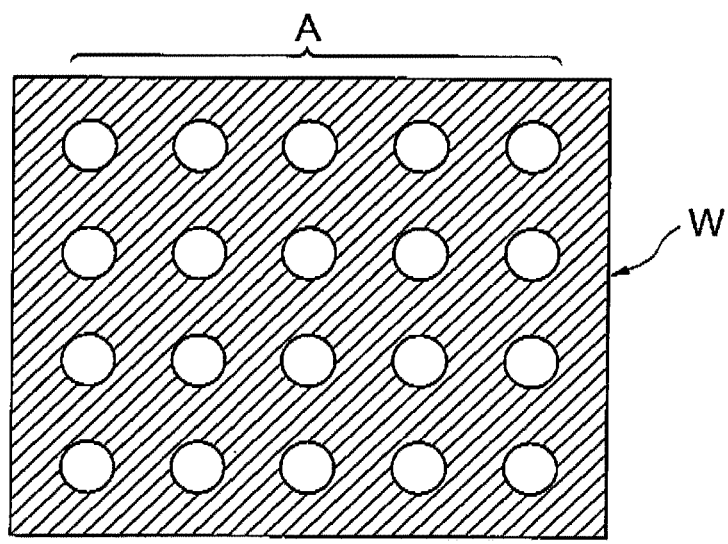
FIG. 3A is an enlarged view of a wafer observed from above.
Figure 3B:
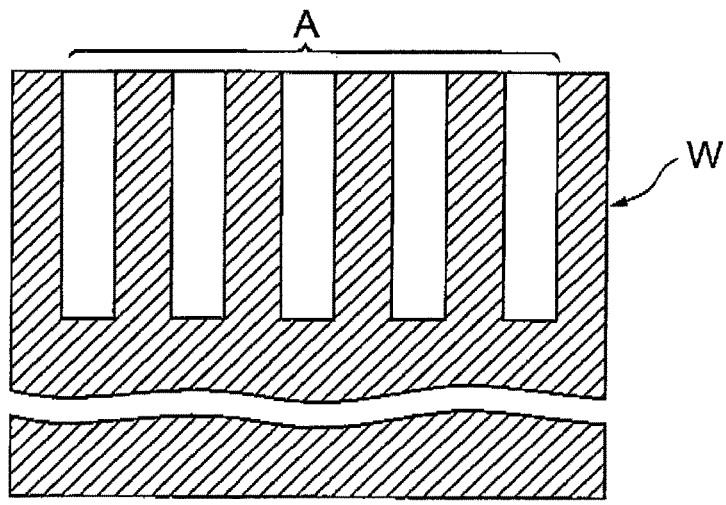
FIG. 3B is an enlarged sectional view of the wafer.

As shown in FIGS. 3A and 3B for example, a repetitive pattern A (a hole pattern) is formed in the surface of the wafer W. Regarding this pattern A, holes (or vias) are regularly arranged in a bare wafer made of silicon (Si). Here, FIG. 3A is an enlarged view of part of the wafer W observed from above, while FIG. 3B is an enlarged sectional view of the wafer W. As an example, the hole diameter is 2 µm, the hole pitch or interval is 4 µm, and the hole depth is 20 µm. Further, the wafer W is 725 µm thick, but FIGS. 3A and 3B illustrate the wafer W omitting the description of its thickness. Further, in FIGS. 3A and 3B, the silicon portion is indicated by oblique (hatched) lines and the holes are indicated by blank or white.

Figure 4A:
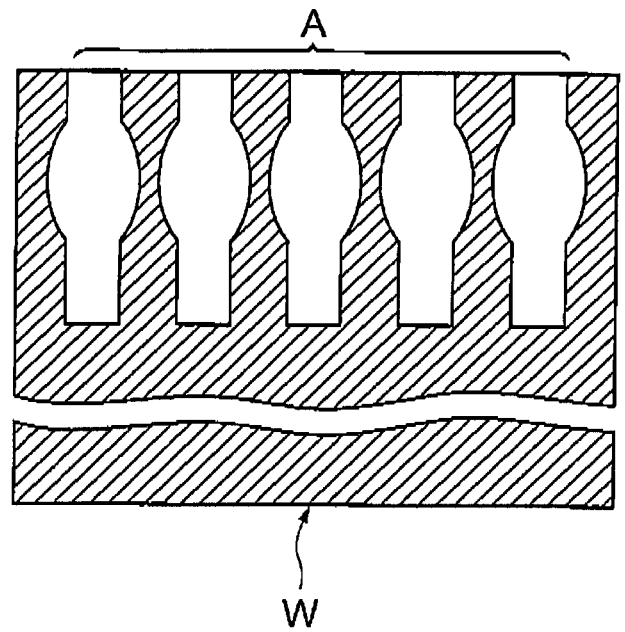
FIG. 4A is an enlarged sectional view of a wafer with the holes swelling out in the middle parts.
Figure 4B:
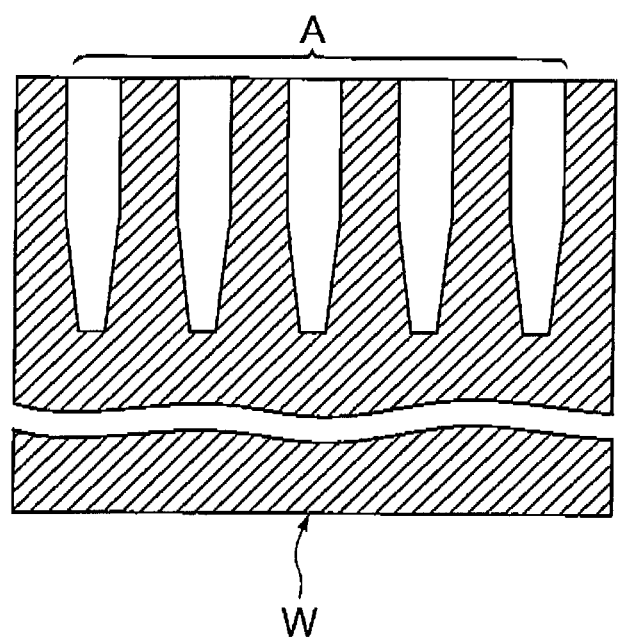
FIG. 4B is an enlarged sectional view of a wafer with the holes tapering off in the deep parts.

FIGS. 4A and 4B show examples of abnormally formed holes which constitutes the pattern A. Here, FIG. 4A shows the holes swelling out in the middle portions thereof, and FIG. 4B shows the holes tapering off in the deep portions thereof. Since such kinds of shapes will give rise to problems in the succeeding forming process and the function of fabricated TSVs, it is necessary to find out definete holes through inspection.

Figure 1:
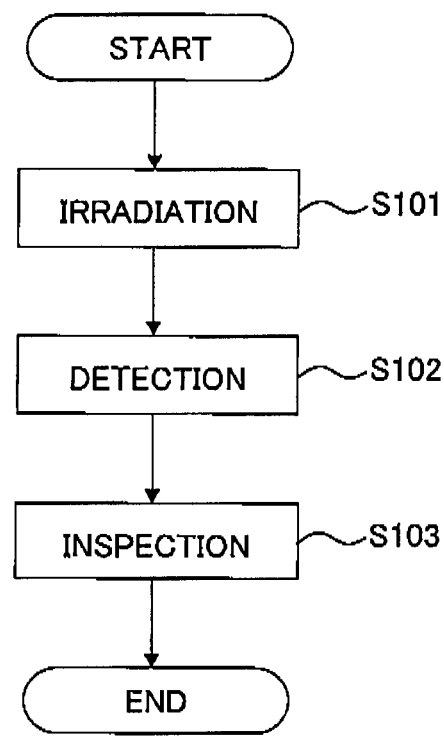
FIG. 1 is a flowchart showing an inspection method.

Referring to the flowchart shown in FIG. 1, explanations will be made with respect to a method for inspecting the wafer W utilizing the inspection apparatus 10 configured in the above manner. Further, the transporting device (not shown) transports in advance the inspection object wafer W onto the wafer holder 15 with its front side directed upward. Further, during the transportation, an alignment mechanism (not shown) obtains positional information of the pattern A formed on the surface of the wafer W, thereby allowing the wafer W to be placed on the wafer holder 15 in a predetermined position along a predetermined direction. Further, the controller 40 sends a command to each part for carrying out the sequence or process stored in a storage device (not shown) to realize the following operations.

First, illumination light transmissive (permeable) for the wafer W is irradiated onto the surface of the wafer W (step S101). In this irradiation step, the illumination light with a predetermined wavelength (in the range of visible or near-infrared light) is emitted from the light source 21 to the illumination-side concave mirror 25, reflected from the illumination-side concave mirror 25 to become parallel light, and irradiated on the entire surface of the wafer W held on the wafer holder 15.

At this time, the imaging device 35 can receive the diffracted light from the repetitive pattern A regularly formed with a predetermined pitch to form an image of the wafer W, by adjusting the wavelength of the illumination light emitted from the light source 21, and the rotation angle and tilt angle of the wafer W held on the wafer holder 15 (to be referred to as satisfying the diffraction condition hereinbelow). In particular, the rotating and tilting mechanism 16 rotates the wafer holder 15 such that the illumination direction on the surface of the wafer W (the direction from the illumination system 20 toward the light receiving system 30) coincide with the repetitive direction of the pattern A. At the same time, the wafer holder 15 is set (the wafer holder 15 is tilted) such that the following expression (1) is satisfied based on Huygens' principle, where P represents the pitch of the pattern A, λ represents the wavelength of the illumination light irradiated on the surface of the wafer W, θ1 represents the incidence angle of the illumination light, and θ2 represents the outgoing angle of the nth-order diffracted light.

$$P = n \times \lambda / \{\sin(\theta 1) - \sin(\theta 2)\} \quad (1)$$

Next, the inspection apparatus 10 detects the diffracted light from the wafer W on which the illumination light is irradiated (step S102). The diffracted light diffracted by the repetitive pattern A of the wafer W is condensed by the light-receiving-side concave mirror 31, and then comes onto the imaging plane of the imaging device 35 to form an image of the wafer W (an image formed by diffracted light). In this detection of the diffracted light, the image sensor of the imaging device 35 generates an image signal by photoelectrically converting the image of the wafer W formed on the imaging plane, and outputs the image signal to the image processing section 45.

Then, the wafer W is inspected by utilizing information of the detected diffracted light (the diffracted light intensity) (step S103). In the inspection of the wafer, the image processing section 45 generates an image of the wafer W (a digital image) based on the image signal inputted from the imaging device 35. Further, after generating the image of the wafer W (the digital image), the image processing section 45 compares the generated image data of the wafer W with the image data of a nondefective wafer stored in the database 46 to inspect whether or not there is any abnormity (defection) in the wafer W. Further, the inspection of the wafer W is carried out according to each chip region. Each of the chip region is determined to be abnormal when the difference between the signal intensity (brightness value) of the inspection object wafer W and the signal intensity (brightness value) of the nondefective wafer is greater than a predetermined threshold value. On the other hand, it is determined to be normal when the difference between the signal intensities (brightness values) is smaller than the threshold value. Then, the inspection result from the image processing section 45 and the image of the wafer W are outputted and displayed on the image display device (not shown).

The inspection apparatus 10 of the first embodiment is utilized to obtain an image based on the diffracted light from the entire surface of the wafer W. Then, the obtained image has a brightness in accordance with the intensity of the diffracted light (to be referred to as a diffraction image hereinbelow). The diffracted light intensity changes according to the distribution of diffraction efficiency. Thus, when the regularly formed pattern A is uniformly laid out, localized change in diffraction efficiency will not occur. On the contrary, when the pattern A changes in profile in some region, then the diffraction efficiency will also change in that region. As a result, the diffraction image in the corresponding region changes in brightness, and thereby it is possible to detect the change of pattern in the corresponding region. Further, the change of pattern refers to, for example, the change of the pattern A in line width (hole diameter) or cross-sectional shape.

The distance or length on the wafer W corresponding to one pixel (pixel size) of the obtained diffraction image taken by the imaging device 35 is, for example, 300 μm, which is much greater than the size of the pattern A and the repetitive pitch. However, the brightness of each pixel in the diffraction image corresponds to an average intensity of the diffracted light from the pattern of the corresponding region on the wafer W. When the pattern A of the wafer W is not normally formed due to some problems with the exposure device and the like for forming the pattern, then the entire pattern of the region occupying a certain area deforms in the same manner. Therefore, even though the pixel size is greater than the size of the pattern A and the repetitive pitch, it is still possible to detect abnormity (defection) of the corresponding region.

For example, when the light source 21 is set so that the light source 21 emits a light beam (illumination light) of the wavelength 546 nm (e-ray) upon receiving the command from the controller 40, and when the diffraction condition is satisfied, then the imaging device 35 can obtain a diffraction image. From this diffraction image, as described hereinbefore, it is possible to detect abnormity (defection) in the pattern A. However, since the light of the wavelength 546 nm is not transmissive through silicon, the detectable abnormities are only those in the vicinity of the surface of the wafer W. That is, the detectable abnormities are those in the hole diameter near the surface of the wafer W, those in the cross-sectional shape of the holes near the surface of the wafer W, and the like.

When the light source 21 is set so that the light source 21 emits a light beam (illumination light) of the wavelength 1100 nm upon receiving the command from the controller 40, and when the diffraction condition is satisfied, then in the same manner a diffraction image can be obtained. However, since the light of the wavelength 1100 nm is transmissive through silicon, it is possible to detect abnormities (defections) even in deep parts of the holes. The light of the wavelength 1100 nm is transmitted through silicon. However, diffracted light (diffraction phenomenon) still arises, because the index of refraction is different between the silicon part and the holes in the wafer W, and the reflected and scattered light beams intensify each other.

In this case, it is possible to find where an abnormity (defection) is located on the surface of the wafer W from the positional information in which brightness has changed in the diffraction image. However, it is difficult to specify in which part the abnormity is located in the depth direction of the hole from the diffraction image.

Figure 5:
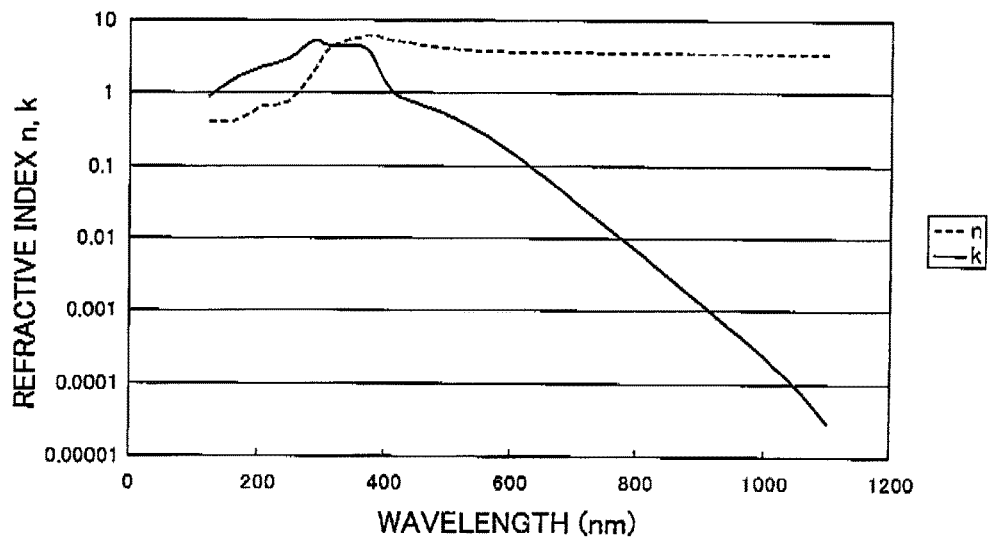
FIG. 5 is a graph showing a change in the complex refractive index of silicon with respect to light wavelength.
Figure 6:
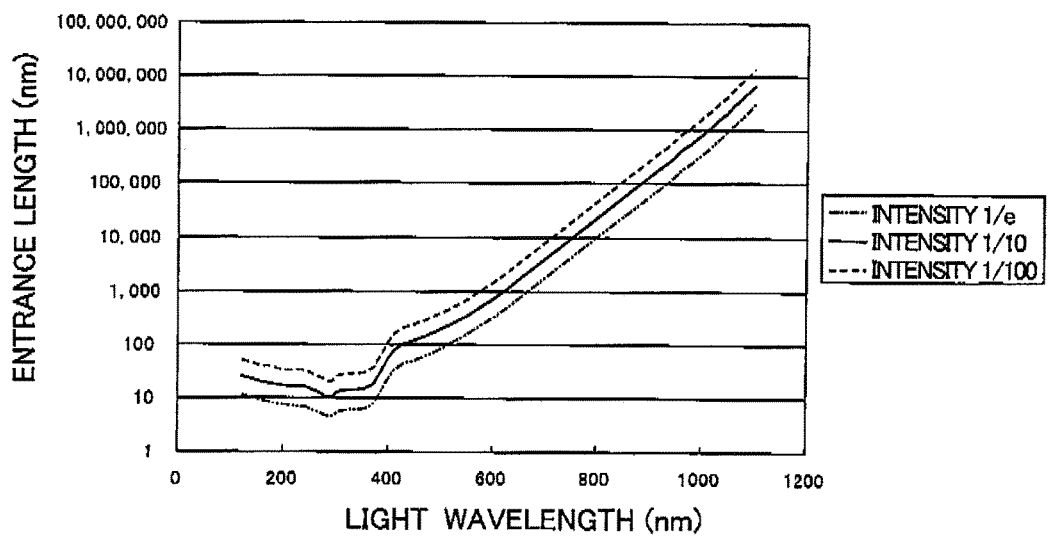
FIG. 6 is a graph showing a change in the entrance length into silicon with respect to light wavelength.

The graph in FIG. 5 shows a change in the complex refractive index of silicon with respect to light wavelength. In the graph in FIG. 5, "n" stands for the real part of the complex refractive index (index of refraction), and k stands for the imaginary part of the complex refractive index (extinction coefficient) and denotes the degree of absorption. The graph in FIG. 6 shows a result of calculating the distance (referred to as the entrance length), based on "k", as the light intensity becomes 1/e, 1/10 and 1/100 due to absorption, respectively, where e is the base of natural logarithm. Further, FIG. 7 shows a result of calculating the wavelength of which extinction coefficient "k" correspond to the distances of 1 μm, 5 μm, 10 μm, 20 μm, 30 μm, etc. at which the light intensity becomes 1/10 due to absorption. That is, it is possible to change the light-reaching depth by altering the illumination wavelength.

In an inspection apparatus configured to be capable of detecting an abnormity (defection) in the part reached by a light beam whose intensity has decayed down to 1/10, it is possible to detect only an abnormity as deep as approximately 1 μm when the light wavelength is 623 nm, for example, while it is possible to detect an abnormity as deep as 30 μm when the light wavelength is 816 nm, and an abnormity as deep as 50 μm when the light wavelength is 845 nm. Therefore, by utilizing these three kinds of wavelengths to carry out the inspection in turn, it is possible to find out an approximate depth of the abnormal portion. It is reasonable to consider that when an abnormity is detected with the light of the wavelength 623 nm, then the abnormity is located in a portion shallower than 1 μm; when an abnormity is detected with the light of the wavelength 816 nm instead of 623 nm, then the abnormity is located in the range of 1 μm to 30 μm; and when an abnormity is detected with the light of the wavelength 845 nm, neither 623 nm nor 816 nm, then the abnormity is located between 30 μm and 50 μm.

Further, in order to make it easy to understand, FIG. 7 shows the values (entrance lengths) with the incident light being vertical with respect to the surface of the wafer W. However, since vertical incidence is not the case with the inspection apparatus 10 of the first embodiment, considering this fact, it is necessary to make correction therefor. Further, the example of FIG. 7 assumes that it is possible to detect an abnormity (defection) where the light intensity becomes 1/10. However, it depends on the sensitivity of the imaging device 35 (image sensor) and the contents of the image processing that determine to what degree the light intensity has decayed until then an abnormity is still detectable. At any rate, by utilizing a plurality of wavelengths different in the transmissivity (for inspection) from each other to carry out the inspection with diffracted light, it is possible to find out where a detected abnormity is located in the depth direction.

In this manner, according to the first embodiment, transmissive illumination light for the wafer W is irradiated onto the surface of the wafer W (the silicon substrate) having the predetermined pattern A formed therein to carry out an inspection for the wafer W utilizing an optical property (diffracted light, for example) with the periodicity of the pattern A. Therefore, the illumination light enters as far as inside the wafer W to make it possible to detect an abnormity (defection) in deep portions of the holes of the pattern A. Therefore, it is possible to carry out the inspection for deep portions of the pattern A in the wafer W.

Further, when the inspection is carried out to a position of a predetermined depth in the wafer W based on the transmissivity (transmission characteristics) of illumination light, it is possible to identify where a detected abnormity is located in the depth direction of the wafer W.

Further, by applying near infrared rays or visible rays as the illumination light, it is possible to utilize an ordinary image sensor to detect the light from the wafer W (to take an image of the wafer W), thereby allowing the inspection to be carried out with a simplified configuration. Further, because near infrared rays may cause the image sensor to decrease its sensitivity and thereby lower the signal to noise ratio, it is possible to use a cooling-type image sensor as necessary to improve the signal to noise ratio.

Further, by inspecting the holes for forming the through-silicon vias (TSVs), it is possible to detect abnormity (defection) in deep portions of the holes, whereby the inspection accuracy can be improved for the through-silicon vias (TSVs).

Further, by utilizing diffracted light to carry out the inspection, even when the pixel size of the wafer W image is greater than the pattern A size and the repetitive pitch, it is still possible to detect abnormity in the relevant region.

Further, when an infrared ray is utilized to inspect the wafer W with TSVs formed therein, problems may arise to affect the inspection such as to undesirably observe the profile of the underneath wafer holder 15, e.g., the grooves for the vacuum chuck due to the transmission of the infrared ray through the wafer W. In order to avoid such problems, the wafer holder 15 may be configured to be a flat member without grooves and the like. By utilizing an electrostatic chuck and the like to electrically attract the wafer, it is possible to flatten the wafer holder 15. Further, by shaping the cross section of the grooves for the vacuum chuck into a gently sloping chevron instead of a rectangle, it is possible to make the grooves indistinct or invisible. On the other hand, even though the wafer holder is an ordinary chuck as it is, it is still possible to prevent the problems from affecting the inspection by refining the illumination wavelength. That is, in the case of carrying out the inspection from one surface of the wafer W with the formed pattern, by selecting an illumination wavelength which reaches as far as the silicon part but is not completely transmitted through in the thickness direction of the wafer W, it is possible to carry out the inspection without letting the wafer holder 15 get in the way. For example, by utilizing the light of the wavelength 976 nm, the distance calculated in the same manner as in the case of FIG. 7 is 500 μm as the light intensity becomes 1/10 due to absorption. According to the first embodiment, when the wafer W is 725 μm thick, it is possible to inspect the TSVs in the surface of the wafer W without seeing through to the wafer holder 15.

Further, although the wafer W of a logic device may have an irregular alignment of TSVs, it is still possible to utilize the above inspection method for the wafer W for QC purpose in such cases. That is, in order to find the setting conditions or confirm accuracy for etching devices and the like, it is possible to evaluate processing uniformity and the like by carrying out the diffraction inspection by utilizing a wafer (a pilot wafer) with a pattern formed with regularly arranged TSVs.

Next, an inspection apparatus in accordance with a second embodiment will be explained. Except for the aspect of holding the wafer W reversely on the wafer holder 15, the inspection apparatus of the second embodiment is configured to be the same as the inspection apparatus 10 of the first embodiment, and each constituting portion is designated by the same reference numeral as in the first embodiment, any detailed explanation of which will be omitted as appropriate (see FIG. 2).

Hereinbelow, explanations will be made with respect to a method for inspecting the wafer W by utilizing the inspection apparatus of the second embodiment. In the second embodiment, a transporting device (not shown) transports in advance the inspection object wafer W onto the wafer holder 15 with its back side directed upward. At the time, a thin-film protection member may be utilized to cover the front side of the wafer W with the formed pattern A to protect the same.

First, in the same manner as the case of the first embodiment, illumination light transmissive for the wafer W is irradiated onto the back side of the wafer W (step S101). In this irradiation of the illumination light, the illumination light with a predetermined wavelength (in the range of visible or near-infrared light) is emitted from the light source 21 to the illumination-side concave mirror 25, reflected from the illumination-side concave mirror 25 to become parallel light, and irradiated on the entire back side of the wafer W held on the wafer holder 15.

Next, still in the same manner as the case of the first embodiment, the inspection apparatus 10 detects the diffracted light from the wafer W on which the illumination light is irradiated (step S102). The illumination light irradiated on the back side of the wafer W reaches as far as the repetitive pattern A on the surface side or front side. The diffracted light arising from this pattern A is condensed by the light-receiving-side concave mirror 31, and then comes onto the imaging plane of the imaging device 35 to form an image of the wafer W (an image formed by diffracted light). In this detection, the image sensor of the imaging device 35 generates an image signal by photoelectrically converting the image of the wafer W formed on the imaging plane, and outputs the image signal to the image processing section 45.

Then, still in the same manner as the case of the first embodiment, the wafer W is inspected by utilizing information of the detected diffracted light (step S103). In this inspection step, the image processing section 45 generates an image of the wafer W (a digital image) based on the image signal inputted from the imaging device 35. Further, after the image of the wafer W (the digital image) is generated, the image processing section 45 compares the generated image data of the wafer W with the image data of a nondefective wafer stored in the database 46 to inspect whether or not there is any abnormality (defection) in the wafer W. Then, the inspection result from the image processing section 45 and the image of that wafer W are outputted and displayed on the image display device (not shown).

In the second embodiment, the wafer W is reversely held on the wafer holder 15 to carry out the diffraction inspection from the surface (the back side) on the opposite side to the surface (the front side) with the formed holes (the pattern A). In an ordinary inspection for the profile of a hole, deep portions and especially the bottom of the hole are often the most important as well as the most difficult portions for inspecting (determining) whether there is any abnormity (defection). It is possible to inspect deep portions of a hole in the first embodiment. However, regarding the information amount of detection, the information about the shallow portion of the hole is more than that about the deep portion. Therefore, the sensitivity is generally decreased for the abnormity (defection) in the deep portion of the hole in comparison with the shallow portion. According to the second embodiment, when the wafer is reversed for the diffraction inspection from the back side, then it is possible to increase the information amount for the deep portion of the hole in comparison with the shallow portion, whereby the deep portion of the hole can be inspected with a high sensitivity. Further, in this case, when the diffraction image is obtained with a plurality of wavelengths different in the transmissivity for the substrate, then it is also possible to know an approximate hole depth by analyzing with which wavelength the diffracted light was detected, and/or by analyzing the signal intensity of each wavelength.

In this manner, according to the second embodiment, in addition to the effect obtained in the first embodiment, it is possible to inspect the deep part of a hole with a high sensitivity.

Further, in the case of carrying out the diffraction inspection from the back side of the wafer W opposite to the surface in which the pattern A is formed, it is possible to polish the back surface of the wafer W into a mirror plane. Further, it is possible to keep the back surface of the wafer W from being contaminated by dirt and the like. Since the illumination light passes through the back surface of the wafer W twice, the inspection can be impeded when the surface is a scattering surface (an unpolished surface), or when dirt and the like adhere to the surface.

Further, by combining the first and second embodiments to carry out the inspection from both front and back sides, it is possible to accomplish a more detailed inspection through the combination of information on the respective depths. Further, in each of the above embodiments, the inspection of the wafer W is carried out by detecting the diffracted light arising from the pattern A of the wafer W. However, the present teaching is not limited to this, but may as well detect a state change of polarized light due to a structural birefringence arising from the pattern A of the wafer W, for example. A state change of polarized light due to a structural birefringence can be detected by arranging polarization elements in the light paths of the illumination system 20 and light receiving system 30, respectively, and adjusting the polarization element of the illumination system 20 and the polarization element of the light receiving system 30 to be a crossed-nicol state. Further, in some cases, the sensitivity may be increased by altering the relation between the polarization elements of the illumination system 20 and light receiving system 30 to deviate from the crossed Nichol state according to the polarization state of reflected light. Further, for example, the inspection apparatus may as well detect the specular light or scattered light from the front side (or the back side) of the wafer W.

Further, for each of the above embodiments, the explanation was made with the example of the wafer W (the silicon substrate) in which the holes to form TSVs are regularly formed. However, the present teaching is not limited to this, but is also applicable to inspections after forming the insulating film and after forming the TSVs, for example.

Further, in each of the above embodiments, a hole pattern is formed in the surface of the wafer W. However, the present teaching is not limited to this but, for example, a line and space pattern may as well be formed. Further, even for a layered (laminated) wafer W, for example, it is still possible to inspect its inner part. Further, compared with pure silicon substrates, ion-implanted silicon substrates vary in light transmissivity. For example, when impurity ions are implanted into the silicon substrate to form a semiconductor, an infrared transmissivity thereof is decreased. In such cases, the wavelength utilized for inspection may be selected, or the amount of illumination light and the like may be adjusted based on the variation of the light transmissivity.

Further, in each of the above embodiments, it is configured to detect the light (to take an image of the wafer W) diffracted on the same side as the illumination light is irradiated. However, the present teaching is not limited to this, but the diffracted light transmitted through the wafer W to the opposite side, the scattered light, the state change of polarized light, etc may be detected. Further, the configuration of those optical systems can be selected based on the thickness of the inspection object substrate, the structure of the pattern, the light transmissivity, the contents of the abnormity (defection) to be detected, and the like.

Further, in each of the above embodiments, the illumination system 20 (light source 21) is configured to irradiate illumination light of a particular wavelength onto the wafer W. However, the illumination system 20 (light source 21) is not limited to this but may be configured to irradiate white light covering the near infrared region onto the wafer W, and then a wavelength selection filter as appropriate may be inserted right before the imaging device 35 in the illumination system 20 to transmit only the light of a particular wavelength (diffracted. light). Further, in each of the above embodiments, the inspection apparatus 10 inspects the entire surface of the wafer W all at one time. However, the present teaching is not necessarily limited to such a configuration but, for example, may divide the inspection of the whole surface of the wafer W into a number of times.

Figure 8:
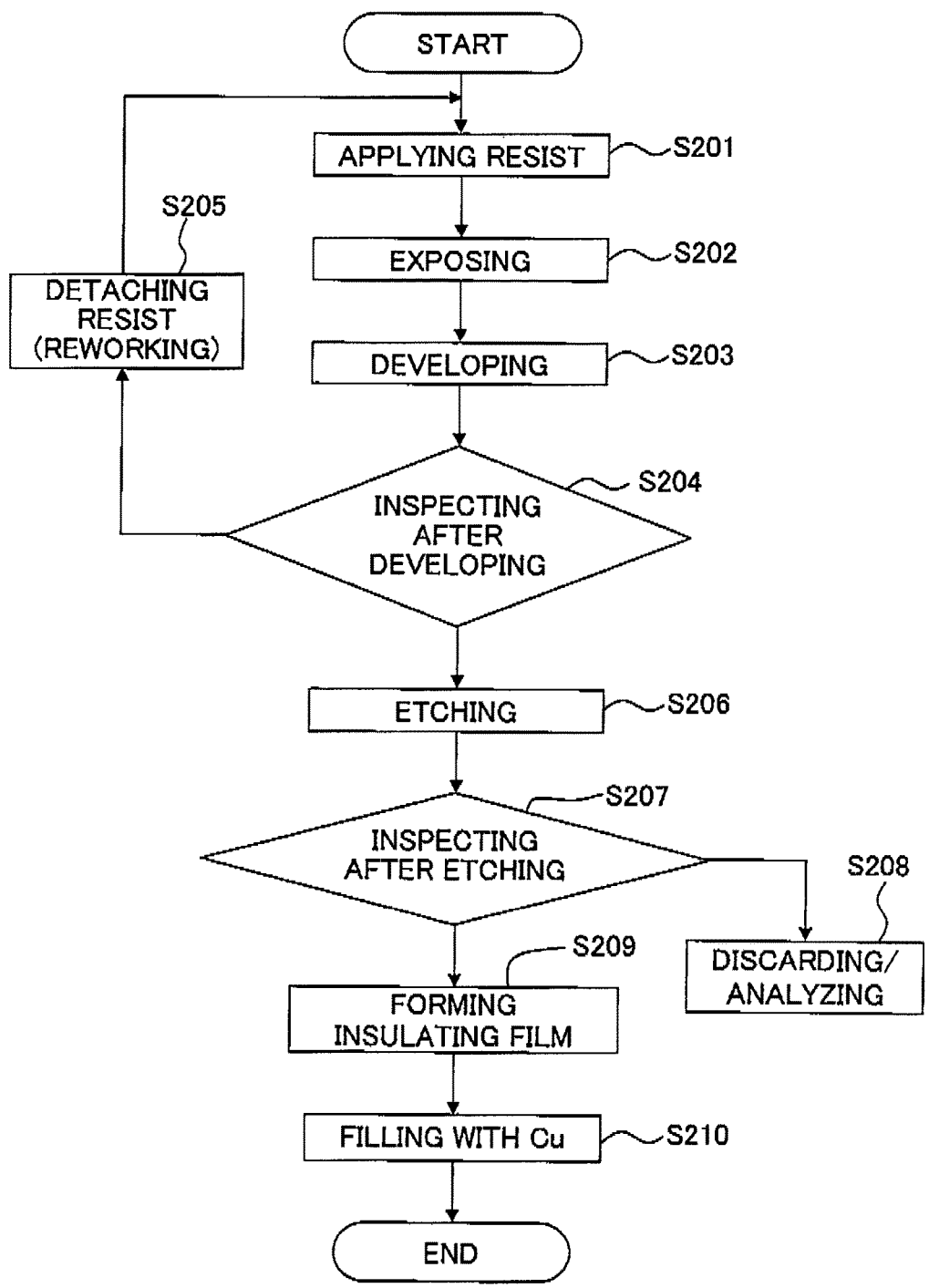
FIG. 8 is a flowchart showing a method for fabricating a semiconductor device.

Next, referring to the flowchart shown in FIG. 8, explanations will be made with respect to a method for producing a semiconductor device while inspecting the wafer W by the inspection method described hereinabove. The flowchart of FIG. 8 shows a process for forming TSVs in a semiconductor device of a three-dimensional lamination type. In this TSV forming process, first, a resist is applied to the surface of a wafer such as a bare wafer and the like (step S201). In this resist application process, a resist application device (not shown) is utilized, for example, to fix the wafer on a rotary support table with a vacuum chuck and the like, and rotate the wafer at a high speed to form a thin resist film after dropping liquid photoresist from a nozzle onto the surface of the wafer.

Next, a predetermined pattern (a hole pattern) is exposed and projected to the wafer surface with the applied resist (step S202). In this exposure process, an exposure device is utilized, for example, to irradiate a light beam of a predetermined wavelength (an energy beam such as an ultraviolet beam and the like) onto the resist of the wafer surface through a photomask with the predetermined pattern formed therein, so as to transfer the mask pattern to the wafer surface.

Next, development is carried out (step S203). In this development process, a developing device (not shown) is utilized, for example, to dissolve the resist in the exposed portion with a solvent, and carry out a process for retaining the resist pattern in the unexposed portion. By virtue of this, the hole pattern is formed in the resist on the wafer surface.

Next, inspection is carried out on the wafer surface with the formed resist pattern or hole pattern (step S204). In the inspection process after development, a surface inspection device (not shown) is utilized, for example, to irradiate illumination light onto the entire wafer surface, take an image of the wafer with the diffracted light arising from the resist pattern, and inspect whether or not there is any abnormity in the resist pattern and the like from the image taken for the wafer. In this inspection process, determination whether or not the resist pattern is nondefective is performed. When it is determined that the resist pattern is defective, it decides whether or not to rework the wafer, i.e., to carry out an action to detach the resist and reprocess the wafer from the resist application. In the case of detecting an abnormity (defection) for which rework is needed, the resist is detached (step S205) and the processes of steps S201 to 5203 are carried out over again. Further, the inspection result from the surface inspection apparatus is fed back to the resist application device, the exposure device, and the developing device, respectively.

If it is confirmed that there is no abnormity in the inspection process after development, then etching is carried out (step S206). In this etching process, an etching device (not shown) is utilized, for example, to mask the retained resist and remove the silicon portion of the underlaying bare wafer to form the holes for forming TSVs. By virtue of this, constituted by the holes for forming TSVs, the repetitive pattern A is formed in the surface of the wafer W.

Next, inspection is carried out on the wafer W with the pattern A formed by etching (step S207). The inspection process after etching is carried out by utilizing the inspection method in accordance with any of the aforementioned embodiments. In this inspection process, when any abnormity is detected, then it is determined how to adjust the exposure condition for the exposure device (a condition of a deformation illumination, a focus offset condition, and the like). Further, it is determined which part of the etching device is to be adjusted, whether to discard the wafer W, or whether it is necessary to further break the wafer W to make a detailed analysis by observing the cross section. These adjustments are performed based on the type and degree of the abnormity which includes information about how deep the determined abnormity has occurred. When a serious and extensive abnormity is discovered in the wafer W after etching, then the wafer W cannot be reworked but is to be discarded or utilized in analysis such as cross section observation and the like (step S208).

When it is confirmed that there is no abnormity found in the inspection process after etching, then an insulating film is formed on the sidewall of the holes (step S209), and the hole portion with the formed insulating film is filled up with Cu (step S210). By virtue of this, TSVs are formed in the wafer (bare wafer).

Further, the inspection result from the inspection process after etching is fed back primarily to the exposure device and the etching device. When some abnormity has been detected in cross-sectional hole profile or in hole diameter, then the feedback is carried out to serve as the information for adjusting the exposure device in focus and dose; when there is some abnormity in hole profile in the depth direction or in hole depth, then the feedback is carried out to serve as the information for adjusting the etching device. In the etching process for forming TSVs, because it is necessary to form the holes with a high aspect ratio (depth/diameter) such as 10 to 20, which is technically difficult, adjustment based on the feedback is important. In this manner, in the etching process, it is required to form deep holes at a nearly vertical angle and, in recent years, a method called RIE (Reactive Ion Etching) is widely adopted. In the case of inspection after etching, it is monitored whether there is any abnormity in the etching device. When some abnormity is detected, then mainly a feedback is performed to shut down and adjust the etching device. As the parameters for adjusting the etching device, for example, these are conceivable: the parameter for controlling the ratio of the etching-rate between the vertical and horizontal directions, the parameter for controlling the depth, the parameter for controlling the uniformity in the wafer surface, and the like.

Further, when the inspection process is carried out after development, then abnormities in the resist application device, exposure device and developing device are basically detected in the inspection process after development. However, when the inspection process is not carried out after development, then when problems in these devices are found out through etching for the first time, feedback to these devices is carried out (to adjust these devices).

On the other hand, it is also possible to feed forward the inspection result from the inspection process after etching to the succeeding processes. For example, when some chips of the wafer W are determined to be. abnormal (defective) in the inspection process after etching, then that information is transmitted from the aforementioned inspection apparatus 10 to the host computer (not shown) for managing processes online and stored therein. Then the stored information may be utilized for management such as not to utilize the abnormal part (chips) in the inspection and measurement of the succeeding processes. Alternatively, the stored information may be utilized to judge whether or not to carry out the wasteful electrical test at the stage of final completion of the device. Further, when the abnormal part is large in area as a result from the inspection process after etching, then it is possible to utilize the information to reduce the influence on the nondefective part by accordingly adjusting the parameter for forming the insulating film or for filling with Cu.

According to the method for producing semiconductor devices in accordance with the present embodiment, because the inspection method in accordance with the aforementioned embodiments is utilized to carry out the inspection process after etching, it is possible to carry out the inspection for deep portions of the pattern A in the wafer W after etching. Therefore, because of the improvement in inspection accuracy, it is possible to improve the efficiency of producing semiconductor devices.

Further, in the aforementioned TSV forming process, TSVs are formed at the initial step before the elements are formed in the wafer. However, the present teaching is not limited to this, but the TSVs may be formed either after the elements are formed or while the elements are being formed. Further, in this case, implanting ions in the process of forming the elements may result in decreasing the degree of transparency for infrared rays but will not lead to complete opaqueness. Therefore, considering the change in transparency, it is practicable to select the wavelength or adjust the amount of illumination light. Further, even on a production line of such type, as a condition provided for the line and for QC purpose, when TSVs are formed in a bare wafer and inspection is carried out, then it is possible to carry out the inspection without being affected by the decrease in transparency due to the ion implantation.

As described hereinbefore, it is possible to feed back the inspection result from the inspection process after etching to the exposure device. Hereinbelow, referring to FIGS. 9 and 10, explanations will be made with respect to an exposure system provided with the aforementioned inspection apparatus 10. This exposure system 100 is configured to include an exposure apparatus 101 which exposes a predetermined pattern (a hole pattern) to project the pattern onto the surface of the wafer W to which a resist is applied, and the inspection apparatus 10 which perform inspection on the wafer W with the pattern A formed in the surface. Then the pattern A is formed in the surface of the substrate through an exposure process with the exposure apparatus 101, a development process with a developing apparatus (not shown), an etching process with an etching apparatus (not shown), and the like.

Figure 9:
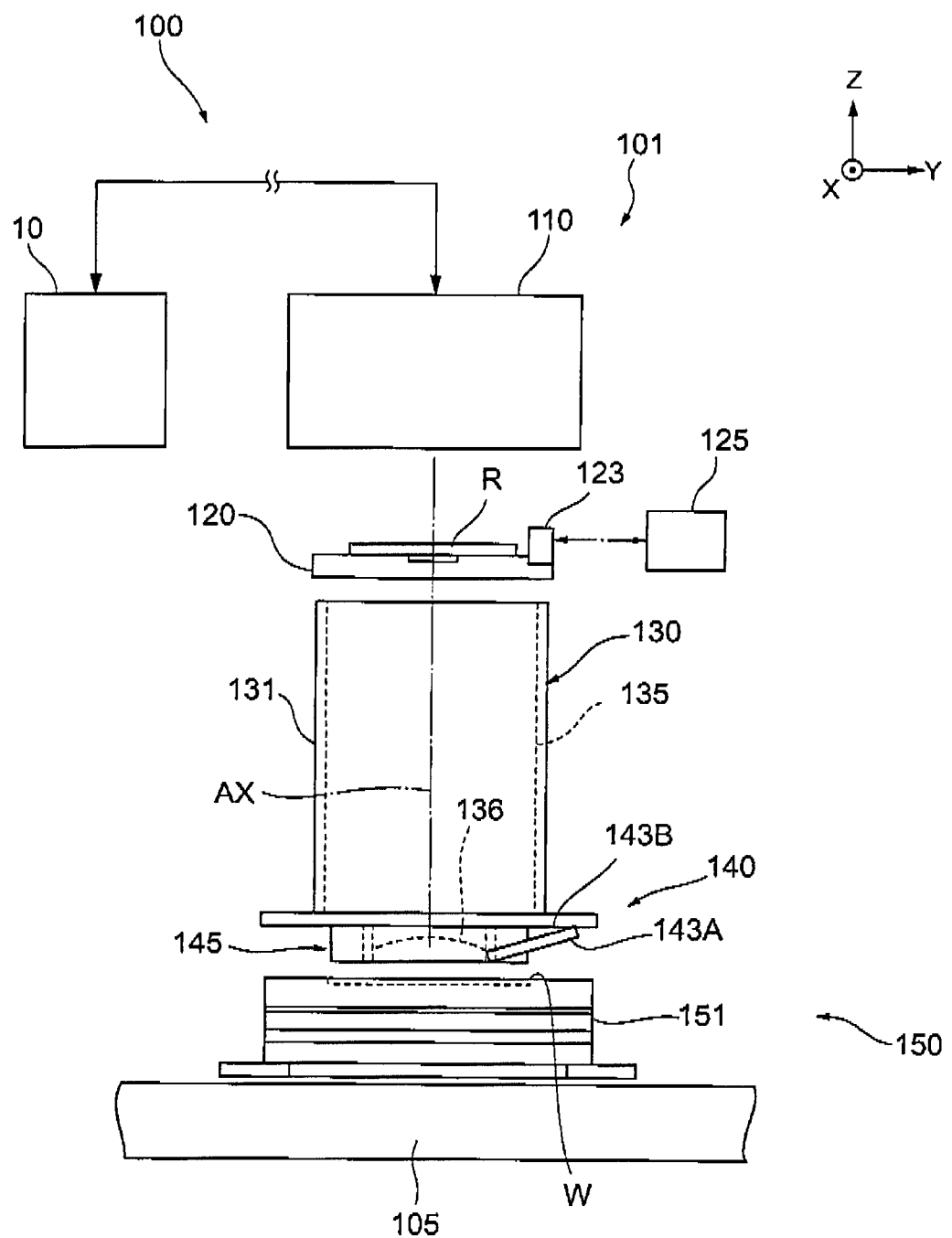
FIG. 9 is a schematic configuration diagram of an exposure system.
Figure 10:
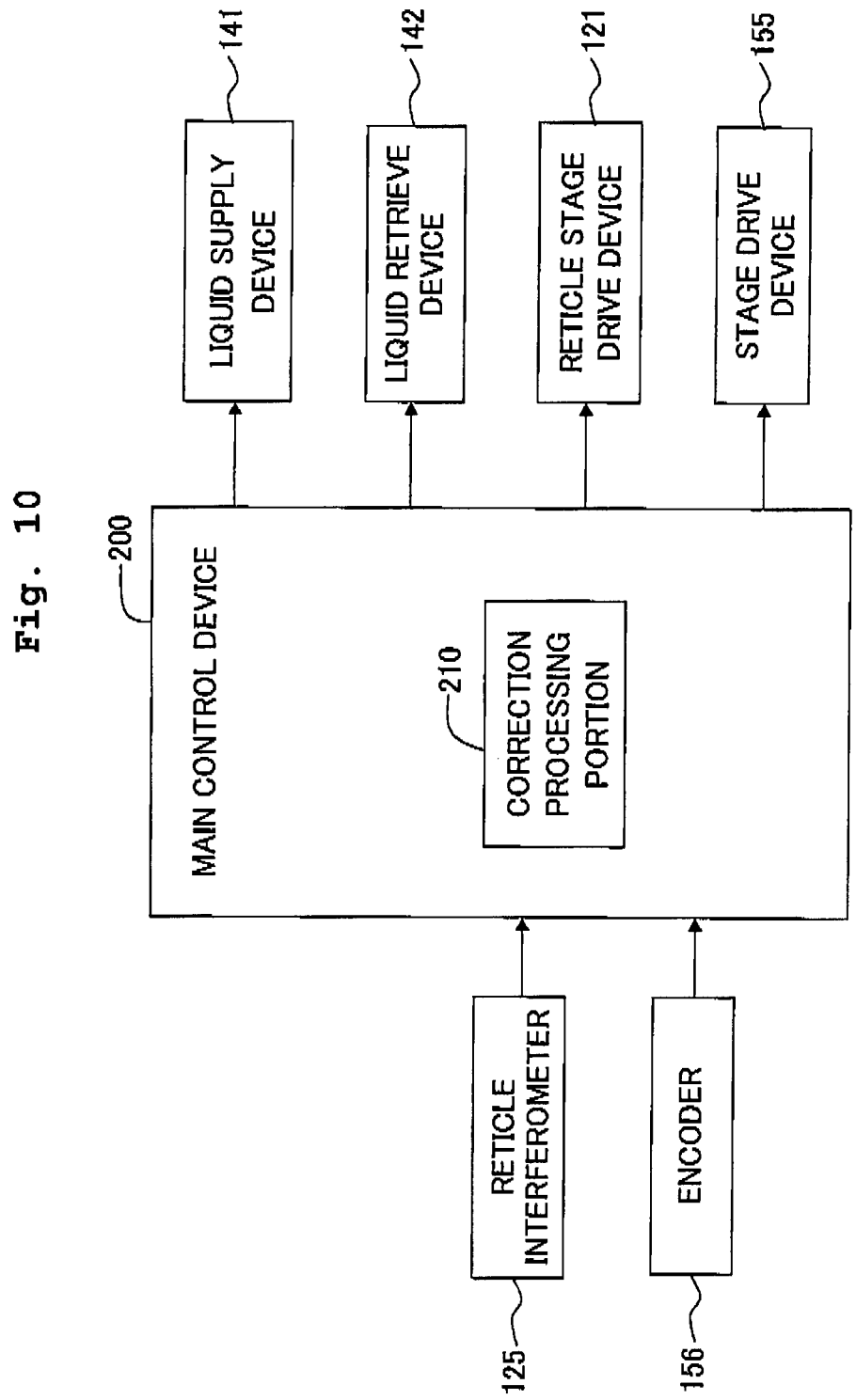
FIG. 10 is a control block diagram of the exposure system.

As shown in FIG. 9, the exposure apparatus 101 is configured to include an illumination system 110, a reticle stage 120, a projection unit 130, a local immersion device 140, a stage device 150, and a main control device 200 (see FIG. 10). Further, in the following explanations, the X-, Y-, and Z-directions shown in FIG. 9 by arrow marks represent an X-axis direction, a Y-axis direction and a Z-axis direction, respectively.

Detailed illustration being omitted, the illumination system 110 has an illuminance uniformized optical system provided with a light source, an optical integrator and the like, and an optical illumination system provided with a reticle blind and the like, and is configured to illuminate a slit-shaped illumination region on a reticle R defined by the reticle blind with an illumination light (exposure light) by an approximately uniform illuminance. As the illumination light, for example, ArF excimer laser light is utilized (wavelength 193 nm).

The reticle R (a photomask) is held on the reticle stage 120 and fixed by vacuum attraction, for example, with a predetermined pattern (a hole pattern, for example) formed in its patterning surface (the lower surface in FIG. 9). The reticle stage 120 is configured to be movable within the X-Y plane by means of a reticle stage drive device 121 (see FIG. 10) provided with a linear motor and the like, for example, as well as to be movable at a predetermined scanning speed in a scanning direction (the Y-axis direction in the present case).

A reticle interferometer 125 detects positional information of the reticle stage 120 in the X-Y plane (including rotational information in the rotation direction about Z-axis) via a first reflector 123 having a reflection surface perpendicular to Y-axis and a second reflector (not shown) having a reflection surface perpendicular to X-axis, provided on the reticle stage 120. The positional information detected by the reticle interferometer 125 is sent to the main control device 200, which controls the position (and the moving speed) of the reticle stage 120 via the reticle stage drive device 121 based on this positional. information.

The projection unit 130 is arranged below the reticle stage 120 and configured to have a lens barrel 131, and an optical projection system 135 held inside the lens barrel 131. The optical projection system 135 is configured to have a plurality of optical elements (lens elements) aligned along the optical axis AX of illumination light, and have a predetermined projection magnification (for example, ¼, ⅕, ⅛, or the like) in a bilateral telecentric. Therefore, when the illumination light emitted from the illumination system 110 illuminates the illumination region on the reticle R, by virtue of the illumination light transmitted through the reticle R arranged such that the objective surface of the optical projection system 135 is approximately consistent with the pattern surface, a diminished pattern image of the reticle R within the illumination region is formed in the exposure region on the wafer W arranged on the imaging plane side of the optical projection system 135 (the region conjugative to the illumination region on the reticle R) via the optical projection system 135. Then, by synchronously driving the reticle stage 120 and the stage device 150 for holding the wafer W, the reticle R is moved in the scanning direction with respect to the illumination region (the Y-axis direction), while the wafer W is also moved in the scanning direction with respect to the exposure region (the Y-axis direction). Accordingly, a scanning exposure is carried out in one shot region on the wafer W, and thus the pattern (mask pattern) of the reticle R is transferred to that shot region.

In the exposure apparatus 101, the local immersion device 140 is provided to carry out exposure in an immersion method. As shown in FIGS. 9 and 10, the local immersion device 140 is configured to have a liquid supply device 141, a liquid retrieve device 142, a liquid supply pipe 143A, a liquid retrieve pipe 143B, and a nozzle unit 145. The nozzle unit 145 is supported by a frame member (an unshown member constituting the exposure apparatus 101) which supports the projection unit 130 in such a manner as enclosing the periphery of the lower end of the lens barrel 131 for holding the optical element closest to the imaging plane (the wafer side) constituting the optical projection system 135, i.e., the foremost lens 136 in the present case. Further, the nozzle unit 145 is set as shown in FIG. 9 such that the lower-end surface of the nozzle unit 145 lies substantially the same plane with the lower-end surface of the foremost lens 136.

Detailed illustration being omitted, the liquid supply device 141 is configured to have a tank which stores the liquid, a pressure pump, a temperature controller, and a valve for regulating the liquid flow rate. The liquid supply device 141 is connected to the nozzle unit 145 through the liquid supply pipe 143A. Again detailed illustration being omitted, the liquid retrieve device 142 is configured to have a tank which stores the retrieved liquid, a suction pump, and a valve for regulating the liquid flow rate, and is connected to the nozzle unit 145 through the liquid retrieve pipe 143B.

As shown in FIG. 10, the main controller 200 controls the operation of the liquid supply device 141 to supply liquid (pure water, for example) to the portion between the foremost lens 136 and the wafer W through the liquid supply pipe 143A. At the same time, the main controller 200 also controls the operation of the liquid retrieve device 142 to retrieve the liquid from the portion between the foremost lens 136 and the wafer W through the liquid retrieve pipe 143B. In this case, the main controller 200 controls the operations of the liquid supply device 141 and liquid retrieve device 142 such that the supplied liquid amount is constantly equal to the retrieved liquid amount. Therefore, between the foremost lens 136 and the wafer W, a certain amount of liquid is constantly exchanged and maintained, whereby an immersion region (immersion space) is formed. In this manner, the exposure device 101 exposes the wafer W by irradiating illumination light onto the wafer W via the liquid forming the immersion region.

The stage device 150 is configured to have a wafer stage 151 arranged below the projection unit 130, and a stage drive device 155 which drives the wafer stage 151 (see FIG. 10). The wafer stage 151 is supported in a levitated manner by an air slide (not shown) above a base member 105 with a clearance of a few micrometers, and configured to hold the wafer W on the upper surface of the wafer stage 151 through vacuum suction. Further, the wafer stage 151 is movable along the upper surface of the base member 105 within the X-Y plane by means of a motor constituting the stage drive device 155.

An encoder 156 (see FIG. 10) detects positional information of the wafer stage 151 in the X-Y plane. The positional information detected by the encoder 156 is sent to the main controller 200, which controls the position (and the moving speed) of the wafer stage 151 via the stage drive device 155 based on this positional information.

In the exposure apparatus 101 configured in the above manner, when the illumination light emitted from the illumination system 110 illuminates the illumination region on the reticle R, a diminished pattern image of the reticle R within the illumination region is formed in the exposure region on the wafer W via the optical projection system 135, by virtue of the illumination light transmitted through the reticle R arranged such that the objective surface of the optical projection system 135 is approximately consistent with the pattern surface. Then, the wafer W is supported on the wafer stage 151 and arranged on the imaging plane side of the optical projection system 135 (the region conjugative to the illumination region on the reticle R). By synchronously driving the reticle stage 120 and the wafer stage 151 for supporting the wafer W, the reticle R is moved in the scanning direction with respect to the illumination region (the Y-axis direction), while the wafer W is also moved in the scanning direction with respect to the exposure region (the Y-axis direction). Accordingly, a scanning exposure is carried out in one shot region on the wafer W, and thus the pattern of the reticle is transferred to that shot region.

In this manner, after the exposure process is carried out with the exposure device 101, then the development process is carried out with the developing device (not shown), and the etching process is carried out with the etching device (not shown) and the like. After those processes, the inspection apparatus 10 in accordance with the aforementioned embodiments carries out the inspection of the wafer W with the pattern A formed in the surface thereof. That is, the inspection process after etching is carried out by utilizing the inspection method in accordance with any of the aforementioned embodiments (or a combination of the inspection methods in accordance with the aforementioned embodiments). The inspection result from the inspection process after etching is fed back primarily to the exposure apparatus 101. At this time, for example, the controller 40 (output section) of the inspection apparatus 10 outputs the information about the inspection result to the exposure apparatus 101 through a connecting cable (not shown) and the like. Then, a correction processing portion 210 provided in the main controller 200 of the exposure apparatus 101 corrects various parameters for setting the exposure apparatus 101 based on the inspection result inputted from the inspection apparatus 10.

By virtue of the above configuration, according the exposure system 100 of the present embodiment, because the setting of the exposure apparatus 101 is corrected based on the inspection result inputted from the inspection apparatus 10 in accordance with the aforementioned embodiments, it is possible to carry out the correction based on the inspection result with a higher accuracy, thereby allowing the exposure apparatus 101 to be set more properly.

Further, in the exposure system 100 described hereinabove, the inspection apparatus 10 in accordance with the aforementioned embodiments inspects the wafer W after etching. However, the present teaching is not limited to this but may inspect the wafer W after development.

Further, the present inventors has prepared a few test wafers and verified the detection sensitivity for various abnormities (defections). In this experiment, the near-infrared light of the wavelength 1100 nm was utilized as the illumination light. Further, the light source was a halogen lamp, and the light of the wavelength 1100 nm was taken out by an interference filter. With respect to the light of the wavelength 1100 nm, the k for silicon (extinction coefficient) is approximately 0.00003, and thus silicon becomes almost transparent with respect to the light of the wavelength 1100 nm. However, for this wavelength, the sensitivity of the image sensor also becomes exceedingly low. Therefore, in order to secure a sufficient S/N ratio (signal-noise ratio), a cooling-type imaging device was utilized. Further, the illumination light rays applied in the experiment had the following wavelengths: 850 nm, 800 nm, 700 nm, 546 nm (e-ray), 436 nm (g-ray), 405 nm (h-ray), and the like.

Figure 11A:
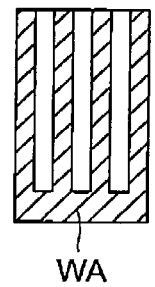
FIG. 11A is an enlarged sectional view of a first test wafer.
Figure 12:
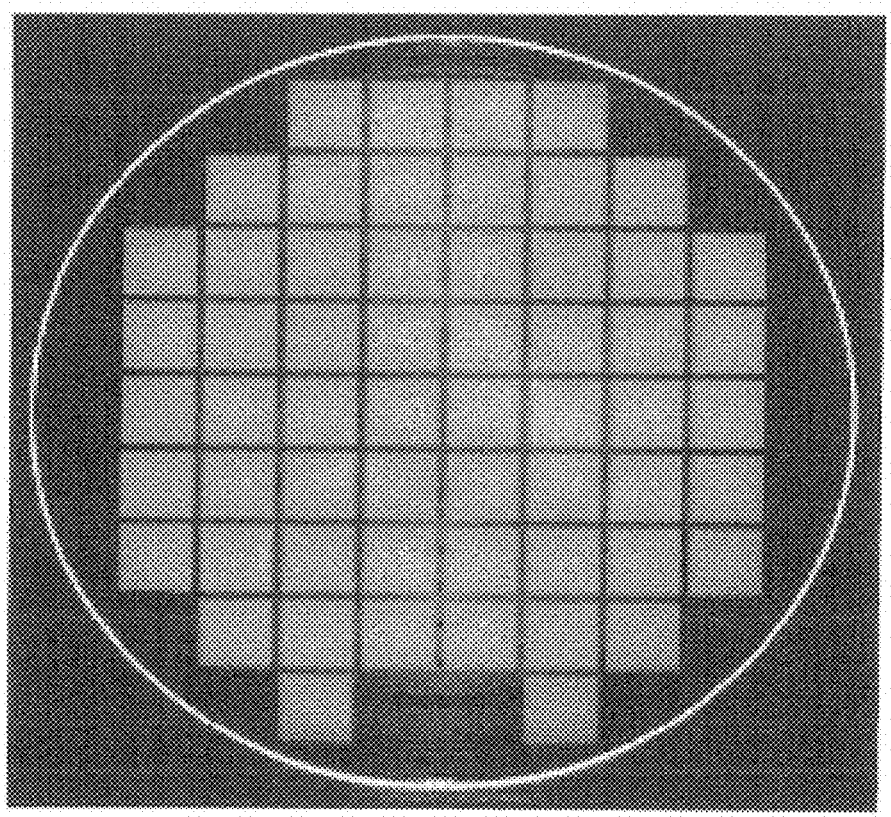
FIG. 12 shows a diffraction image of the first test wafer.

The wafer shown in FIG. 11A (to be called a first test wafer WA hereinbelow) had a pattern (a hole pattern) formed in a standard shape. FIG. 12 shows a diffraction image of the first test wafer WA based on the fourth-order diffracted light from the illumination light of the wavelength 1100 nm. The diffraction image of the first test wafer WA was taken by capturing the uniform diffracted light from the pattern.

Figure 11B:
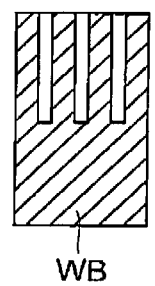
FIG. 11B is an enlarged sectional view of a second test wafer.
Figures 13A, 13B:
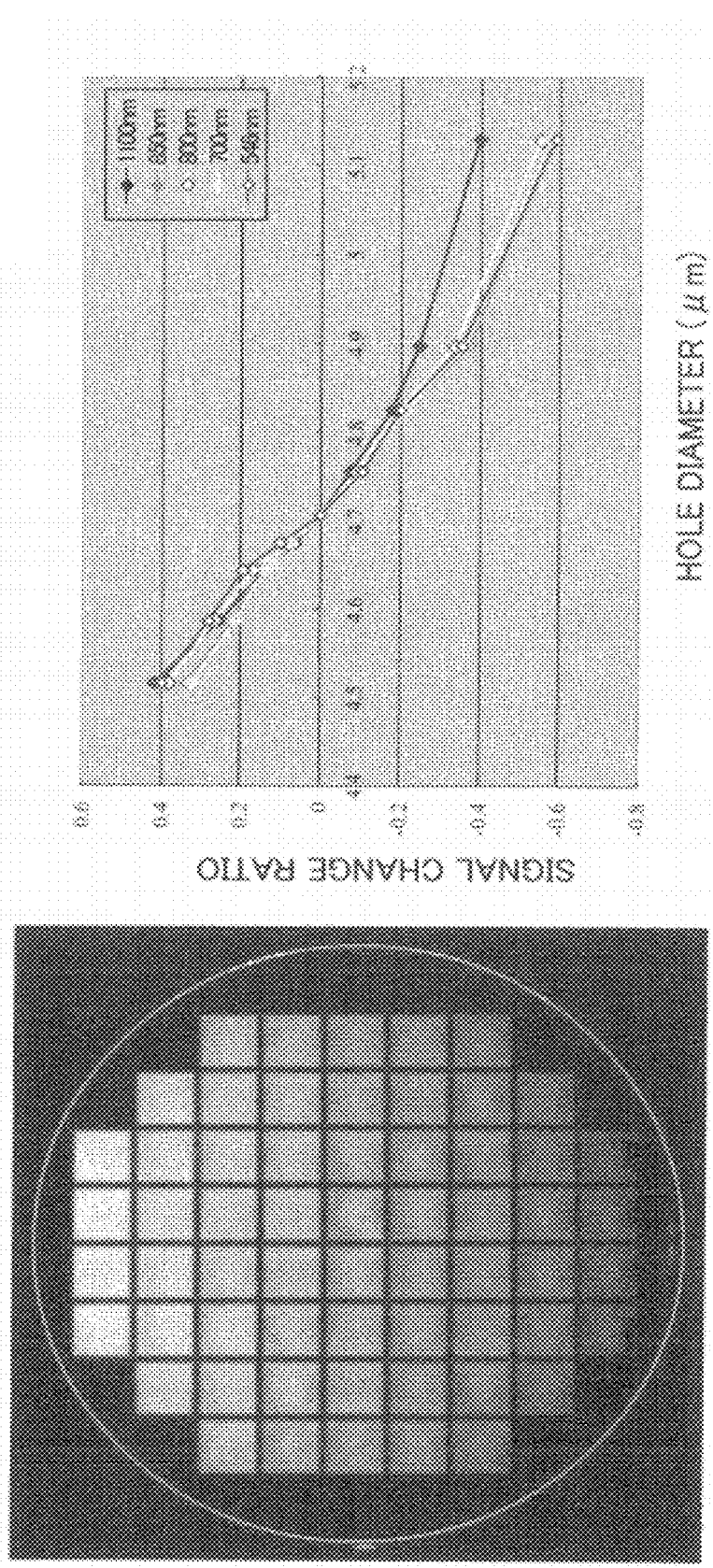
FIG. 13A shows a diffraction image of the second test wafer.
FIG. 13B is a graph showing a relationship between the signal intensity in the diffraction image of FIG. 13A and the hole diameter.

The wafer shown in FIG. 11B (to be called a second test wafer WB hereinbelow) was produced by changing the dose within the wafer surface in exposing the hole pattern to vary the hole diameter according to each shot. Further, the diameter of the holes formed through etching (the diameter of the vias) also varied with the change of dose in amount. Further, the hole diameter was not uniform even within the same shot plane. FIG. 13A shows a diffraction image of the second test wafer WB based on the second-order diffracted light from the illumination light of the wavelength 546 nm (e-ray). In FIG. 13A, the shot arrangement is such that the hole diameter becomes smaller toward the upper part of the figure, but becomes greater toward the lower part of the figure. Further, a CD-SEM measured the hole diameter of each shot in advance. Further, FIG. 13B shows a relationship between the hole diameter and the intensity change of diffracted light (the change of signal intensity), where the vertical axis of the graph stands for the change ratio of the signal intensity and the horizontal axis stands for the hole diameter.

As understood from FIGS. 13A and 13B, the diffracted light intensity (signal intensity) varies almost linearly with the change of the hole diameter. That is, it is possible to detect a change in hole diameter from a light intensity change of the diffraction image. Further, the least square method may be utilized to find the relational expression between the diffracted light intensity (signal intensity) and the hole diameter (a linear approximate expression, for example) in advance. Then, a calculation section may be provided in the inspection apparatus 10 which finds the hole diameter from the signal intensity of diffraction image by utilizing the relational expression obtained earlier. Further, a new step may be added in inspecting the wafer W for finding the hole diameter with the calculation section. By virtue of this, it is possible to find the hole diameter from the diffraction image of the wafer W. Further, the calculation section may either make use of the computing circuit such as the CPU and the like included in the controller 40, the image processing section 45 and the like, or be provided independently of the controller 40, the image processing section 45 and the like.

Figures 14A, 14B, 14C:
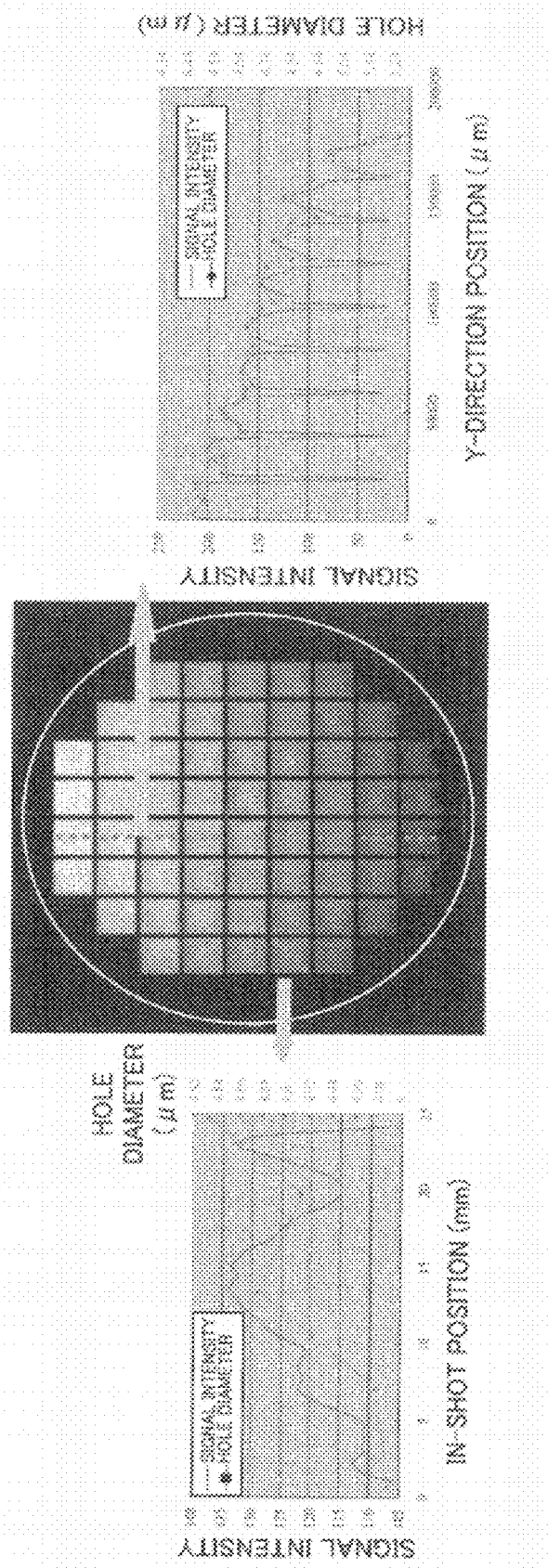
FIG. 14A shows the diffraction image of the second test wafer.
FIGS. 14B and 14C are graphs comparing respective correlations between the signal intensity in the diffraction image of FIG. 14A and the hole diameter.

Further, FIG. 14A shows the same diffraction image as FIG. 13A, and FIGS. 14B and 14C show results of comparing the correlation between the signal intensity in the diffraction image and the hole diameter. In FIG. 143, the vertical axis of the graph stands for the signal intensity or the hole diameter, and the horizontal axis stands for the Y-direction position in the wafer plane (the vertical direction of FIG. 14A). Further, in FIG. 14C, the vertical axis of the graph stands for the signal intensity or the hole diameter, and the horizontal axis stands for the in-shot position in the diagonal direction. As understood from FIGS. 14B and 14C, a strong correlation is present between the signal intensity in the diffraction image and the hole diameter.

Figure 11C:
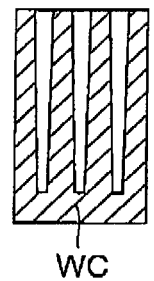
FIG. 11C is an enlarged sectional view of a third test wafer.
Figure 15:
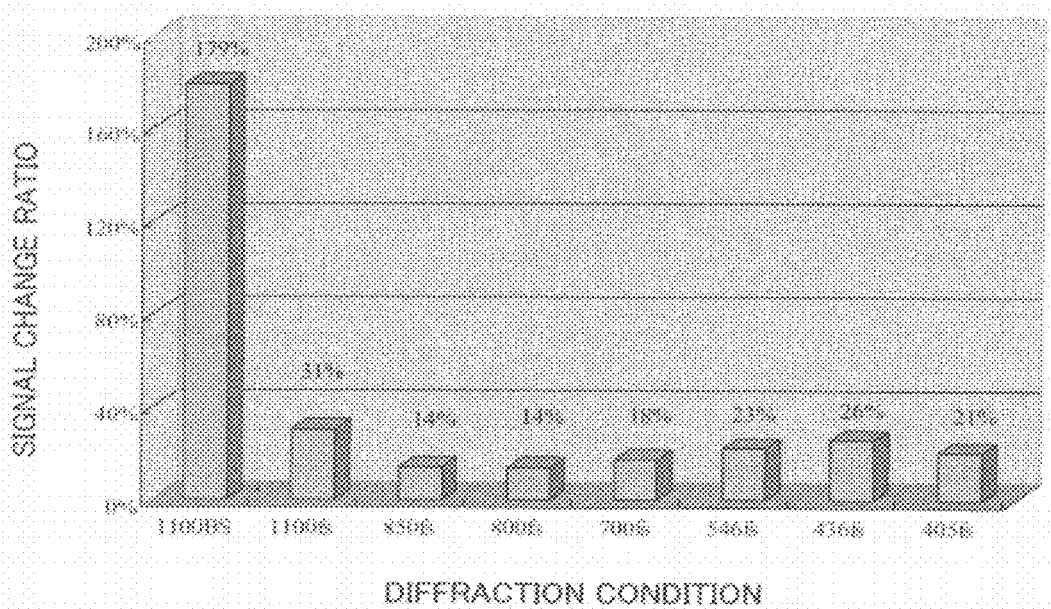
FIG. 15 is a graph showing a signal change with respect to the change in pattern from the first test wafer to the third test wafer.

The wafer shown in FIG. 11C (to be called a third test wafer WC hereinbelow) is such that the diameter of the hole opening is almost the same as that of the first test wafer WA, and the deeper the hole the smaller the diameter. The graph of FIG. 15 compares the diffracted light intensities (signal intensities) from the point of view of detecting the pattern profile transforming from that of the first test wafer WA to that of the third test wafer WC. In the graph of FIG. 15, 1100 BS represents the signal change in inspecting the diffraction from the back side of the wafer with the illumination light of the wavelength 1100 nm, and 1100 fs (850 fs, 800 fs, etc.) represents the signal change in inspecting the diffraction from the front side of the wafer with the illumination light of the wavelength 1100 nm (850 nm, 800 nm, etc.), where "BS" is the abbreviation for back side, indicating the diffraction from the back side of the wafer, while "fs" is the abbreviation for front side, indicating the diffraction from the front side of the wafer, and the same is true with FIG. 17. Further, in FIG. 15, the signal change ratios are illustrated by taking the signal intensity of first test wafer WA as 100%, respectively. In the diffraction inspection from the front side of the wafer, the greatest signal change rate is 31% with the illumination light of the wavelength 1100 nm. On the other hand, in the diffraction inspection from the back side of the wafer, the signal change ratio is 179% obtained with the illumination light of the wavelength 1100 nm. It is evident that in inspecting abnormity in the vicinity of the deep end of the holes, the diffraction inspection from the back side of the wafer is most effective.

Figures 16A, 16B:
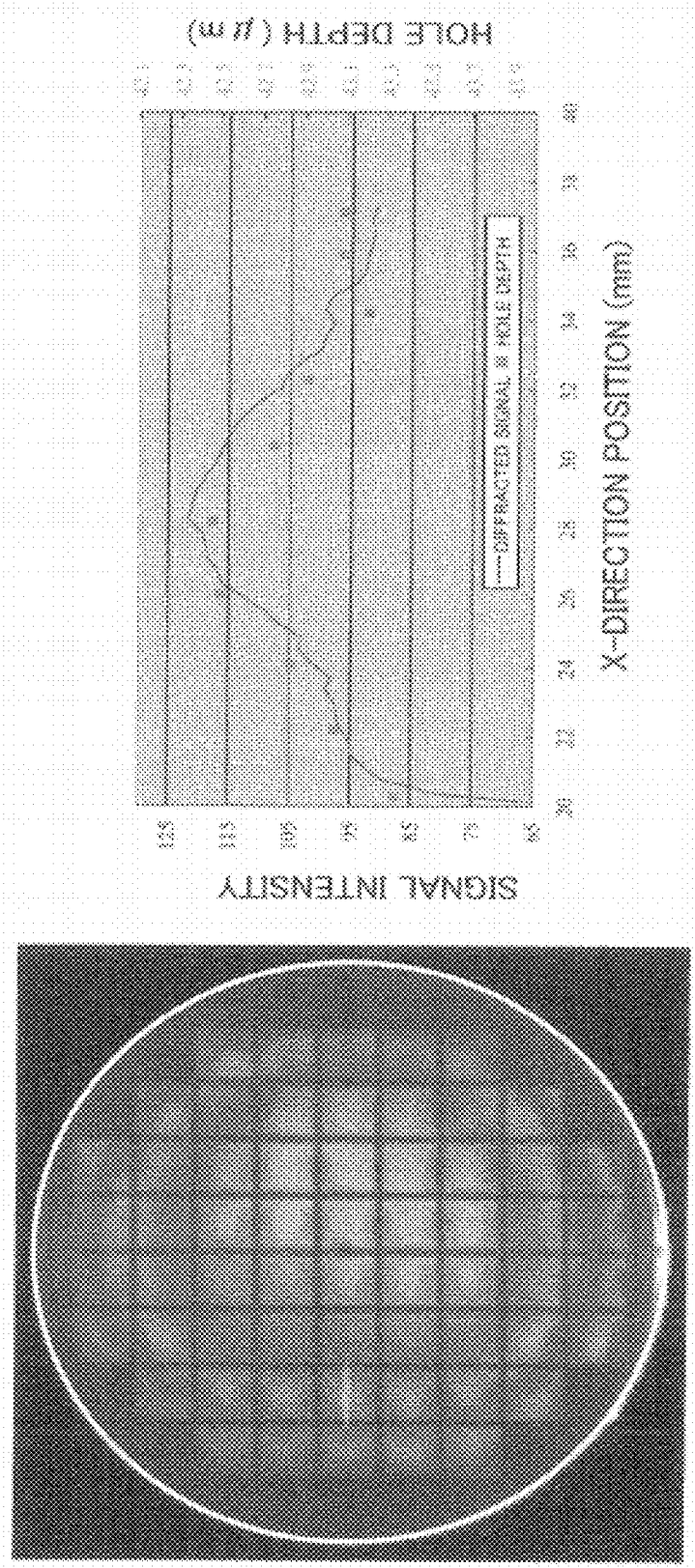
FIG. 16A shows a diffraction image of a wafer fabricated under the same condition as for the first test wafer.
FIG. 16B is a graph showing a correlation between the signal intensity in the diffraction image of FIG. 16A and the hole depth.

On the other hand, FIG. 16A is a diffraction image of another test wafer produced under the same condition as for the first test wafer WA based on the fourteenth-order diffracted light from the illumination light of the wavelength 1100 nm. A characteristic donut-shaped nonuniformity is present in this image. The wafer is transected along an X-direction line through the center of the wafer (the horizontal direction of the figure) for observing the cross section of the wafer with a SEM and comparing the hole depth (via depth) and the diffracted light intensity (signal intensity). As a result, from the comparison of the in-shot profile along the white line of FIG. 16A, a correlation with the hole depth has been proved as shown in FIG. 16B, where the vertical axis of the graph stands for the signal intensity or the hole depth, and the horizontal axis stands for the in-shot position in the X-direction (the horizontal direction of the figure). However, because the diffracted signal also responds to other changes in profile than the change in hole depth, the donut-shaped nonuniformity of FIG. 16A can be regarded as the nonhomogeneity captured in the wafer surface combining various changes in profile due to the "Deep RIE" (RIE: Reactive Ion Etching).

Figure 11D:
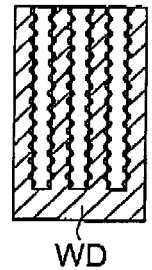
FIG. 11D is an enlarged sectional view of a fourth test wafer.
Figure 17:
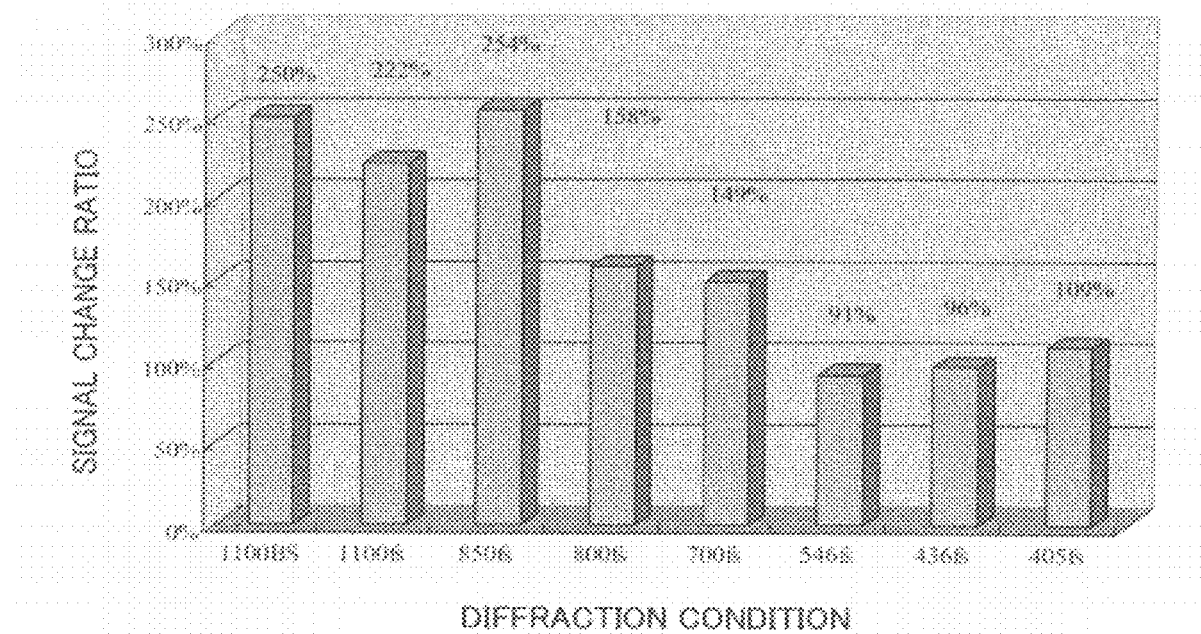
FIG. 17 is a graph showing a signal change with respect to the change in pattern from the first test wafer to the fourth test wafer.

The detection sensitivity for the sidewall roughness has also been verified. Although the "Bosch process" can serve as an etching method for forming holes with a high aspect ratio, this method causes a characteristic concentric grading to occur easily in the sidewall of the holes. This may become an obstacle for forming TSVs, depending on the degree of the sidewall roughness. The fourth test wafer WD shown in FIG. 11D has such a grading which is artificially made. FIG. 17 shows the signal changes with respect to the pattern change from the first test wafer WA to the fourth test wafer WD. Further, FIG. 17 shows the signal change rates by taking the signal intensity of the first test wafer WA as 100%, respectively. Further, in this combination of the test wafers, since change occurs not only in the sidewall roughness but also in the cross section or profile, the signal change is observed collectively with respect to the both aspects. As understood from FIG. 17, there is a tendency that the longer the wavelength of the illumination light, the greater the signal change.

What is claimed is:

1. A method for inspecting a substrate comprising:
    irradiating infrared light of a plurality of different wavelengths onto a first surface or a second surface opposite to the first surface, of the substrate in which a pattern having a periodicity and extending from the first surface to an inside of the substrate is formed in the first surface, each of the plurality of different wavelengths of the infrared light having a permeability to permeate the substrate to a respective predetermined depth;
    detecting, with respect to each of the wavelengths, a diffracted light diffracted by the pattern of the substrate, or a polarization component of light transmitted through the substrate; and
    inspecting the substrate up as far as the predetermined depths based on detection results of the wavelengths regarding the diffracted light diffracted by the pattern of the substrate, or the polarization component of the light transmitted through the substrate,
    wherein at least one of an incidence angle of the infrared light with respect to the substrate and an exit angle of the diffracted light or the transmitted light with respect to the substrate is changed in accordance with the plurality of different wavelengths.

2. The method for inspecting the substrate according to claim 1, wherein the substrate is a silicon substrate; and upon inspecting the substrate, the silicon substrate is inspected up to a first depth by a detection signal from the silicon substrate that is detected during the detection of the light, based on the permeability of the infrared light to the silicon substrate.

3. The method for inspecting the substrate according to claim 1, wherein a wavelength of the infrared ranges from approximately 600 nm to approximately 1100 nm.

4. The method for inspecting the substrate according to claim 1, wherein the pattern is a hole pattern in which a plurality of holes is formed in the substrate to provide through electrodes in the substrate.

5. The method for inspecting the substrate according to claim 4, further comprising calculating a diameter of the holes from a detection signal obtained during the detection of the light, based on a correlation between the light from the substrate and the diameter of the holes.

6. The method for inspecting the substrate according to claim 1, wherein upon irradiating the infrared light, the infrared light is irradiated onto the substrate such that diffracted light is occurred from the pattern of the substrate; and upon detecting the light reflected from or transmitted through the substrate, the diffracted light occurred from the pattern by the irradiation of the infrared light onto the substrate is detected.

7. The method for inspecting the substrate according to claim 1, wherein upon detecting the light reflected from the substrate, the infrared light which has at least the permeability to reach the pattern is irradiated, as the infrared light, from the second surface.

8. The method for inspecting the substrate according to claim 1, wherein irradiating the infrared light by utilizing an infrared light with a plurality of wavelengths having different permeabilities from each other, detecting the light with one of the wavelengths reflected from or transmitted through the substrate, and inspecting the substrate are repeated with respect to each of the plurality of wavelengths of the infrared light.

9. The method for inspecting the substrate according to claim 1, wherein a wavelength of the infrared light is changed based on a depth, of the substrate, to be inspected.

10. The method for inspecting the substrate according to claim 1, wherein a position of a defect of the substrate in depth is determined based on each of the results of the detection of the infrared light of the plurality of wavelengths.

11. The method for inspecting the substrate according to claim 1, wherein inspecting the substrate at the predetermined depth is performed by comparing the results of the detection of the infrared light of the plurality of wavelengths and a reference data obtained from an inspection of a non-defective substrate.

12. The method for inspecting the substrate according to claim 1, wherein the infrared light reflected from or transmitted through the substrate due to irradiation of the infrared light is diffracted light diffracted by a pattern formed in the substrate.

13. The method for inspecting the substrate according to claim 1, wherein the inspection of the substrate is performed for each of the plurality of wavelengths in order to identify location of an abnormity in depth.

14. The method for inspecting the substrate according to claim 1, wherein the light amount of the infrared light irradiated onto the substrate is adjusted based on a condition of the substrate.

15. The method for inspecting the substrate according to claim 1, wherein the inspection of the substrate is performed at a plurality of depths based on the detection results of the wavelengths regarding the diffracted light diffracted by the pattern of the substrate, or the polarization component of the light transmitted through the substrate.

16. The method for inspecting the substrate according to claim 1,
    wherein the detection, with respect to each of the wavelengths, is further performed by detecting a polarization component of light reflected from the substrate, and
    the inspection of the substrate is further performed based on detection results of the wavelengths regarding the polarization component of the light reflected from the substrate.

17. The method for inspecting the substrate according to claim 1, wherein the inspection of the substrate is further performed based on detection results of the wavelengths regarding the polarization component of the light reflected from the substrate.

18. The method for inspecting the substrate according to claim 1,
    wherein the detection, with respect to each of the wavelengths, is further performed by detecting a specular light from the substrate, and
    the inspection of the substrate is further performed based on detection results of the wavelengths regarding the specular light from the substrate.

19. The method for inspecting the substrate according to claim 1,
- wherein the detection, with respect to each of the wavelengths, is further performed by detecting a scattered light from the substrate, and
- the inspection of the substrate is further performed based on detection results of the wavelengths regarding the scattered light from the substrate.

20. A method for producing a semiconductor device, the method comprising:
- exposing a predetermined pattern on a surface of a substrate;
- etching the surface of the substrate according to the exposed pattern; and
- inspecting the substrate up as far as a plurality of predetermined depths with the pattern formed in the surface through the exposing or etching,
  - wherein the inspection of the substrate at each of the plurality of predetermined depths is performed based on detection results of a plurality of wavelengths regarding a diffracted light diffracted by the pattern of the substrate, or a polarization component of light transmitted through the substrate, each of the detection being due to irradiation of infrared light of one of the plurality of wavelengths, each of the plurality of wavelengths having a permeability to permeate the substrate to each of the plurality of predetermined depths, respectively, and
  - wherein at least one of an incidence angle of the infrared light with respect to the substrate and an exit angle of the diffracted light or the transmitted light with respect to the substrate is changed in accordance with the plurality of different wavelengths.

21. The method for producing the semiconductor device according to claim 20, wherein the inspection of the substrate is performed for each of the plurality of wavelengths in order to identify location of an abnormity in depth.

22. The method for producing the semiconductor device according to claim 20, wherein the light amount of the infrared light irradiated onto the substrate is adjusted based on a condition of the substrate.

23. The method for producing the semiconductor device according to claim 20, wherein the inspection of the substrate is performed at a plurality of depths based on the detection results of the wavelengths regarding the diffracted light diffracted by the pattern of the substrate, or the polarization component of the light transmitted through the substrate.

24. A method for inspecting a substrate comprising:
- irradiating infrared light of a plurality of different wavelengths onto a first surface or a second surface opposite to the first surface, of the substrate in which a pattern having a periodicity and extending from the first surface to an inside of the substrate is formed in the first surface, each of the plurality of different wavelengths of the infrared light having permeability to permeate the substrate to a respective predetermined depth to be inspected;
- detecting, with respect to each of the wavelengths, a diffracted light diffracted by the pattern of the substrate, or a polarization component of light transmitted through the substrate; and
- inspecting the substrate up as far as the predetermined depths based on detection results of the wavelengths regarding the diffracted light diffracted by the pattern of the substrate, or the polarization component of the light transmitted through the substrate,
- wherein the wavelengths of the infrared light are changed based on the depths to be inspected, and
- wherein at least one of an incidence angle of the infrared light with respect to the substrate and an exit angle of the diffracted light or the transmitted light with respect to the substrate is changed in accordance with the plurality of different wavelengths.

25. The method for inspecting the substrate according to claim 24, wherein the infrared light includes wavelength components from approximately 600 nm to approximately 1100 nm.

26. The method for inspecting the substrate according to claim 24, wherein the inspection of the substrate is performed for each of the plurality of wavelengths in order to identify location of an abnormity in depth.

27. The method for inspecting the substrate according to claim 24, wherein the light amount of the infrared light irradiated onto the substrate is adjusted based on a condition of the substrate.

28. The method for inspecting the substrate according to claim 24, wherein the inspection of the substrate is performed at a plurality of depths based on the detection results of the wavelengths regarding the diffracted light diffracted by the pattern of the substrate, or the polarization component of the light transmitted through the substrate.

29. The method for inspecting the substrate according to claim 24,
- wherein the detection, with respect to each of the wavelengths, is further performed by detecting a polarization component of light reflected from the substrate, and
- the inspection of the substrate is further performed based on detection results of the wavelengths regarding the polarization component of the light reflected from the substrate.

30. The method for inspecting the substrate according to claim 24,
- wherein the detection, with respect to each of the wavelengths, is further performed by detecting a specular light from the substrate, and
- the inspection of the substrate is further performed based on detection results of the wavelengths regarding the specular light from the substrate.

31. The method for inspecting the substrate according to claim 24,
- wherein the detection, with respect to each of the wavelengths, is further performed by detecting a scattered light from the substrate, and
- the inspection of the substrate is further performed based on detection results of the wavelengths regarding the scattered light from the substrate.

* * * * *